US011738000B2

(12) United States Patent
Zhang et al.

(10) Patent No.: US 11,738,000 B2
(45) Date of Patent: Aug. 29, 2023

(54) HYDROQUINONE COMPOUNDS, PREPARATION METHODS THEREFOR, AND USE IN ANTI-TUMOR OR IMMUNOMODULATION THERAPY

(71) Applicants: Biomedical Analysis Center, Academy Of Military Medical Sciences, Beijing (CN); Institute Of Pharmacology And Toxicology, Academy Of Military Medical Sciences, Beijing (CN)

(72) Inventors: Xuemin Zhang, Beijing (CN); Xinhua He, Beijing (CN); Tao Zhou, Beijing (CN); Zhenggang Liu, Beijing (CN); Tao Li, Beijing (CN)

(73) Assignees: BIOMEDICAL ANALYSIS CENTER, ACADEMY OF MILITARY MEDICAL SCIENCES, Beijing (CN); INSTITUTE OF PHARMACOLOGY AND TOXICOLOGY, ACADEMY OF MILITARY MEDICAL SCIENCES, Beijing (CN)

( * ) Notice: Subject to any disclaimer, the term of this patent is extended or adjusted under 35 U.S.C. 154(b) by 224 days.

(21) Appl. No.: 16/988,525

(22) Filed: Aug. 7, 2020

(65) Prior Publication Data

US 2021/0008022 A1 Jan. 14, 2021

Related U.S. Application Data

(62) Division of application No. 16/069,814, filed as application No. PCT/CN2017/074386 on Feb. 22, 2017, now Pat. No. 10,786,481.

(30) Foreign Application Priority Data

Jan. 20, 2016 (CN) .......................... 201610037849.5

(51) Int. Cl.
| | | |
|---|---|---|
| A61K 31/09 | (2006.01) | |
| A61K 31/23 | (2006.01) | |
| A61K 31/325 | (2006.01) | |
| C07C 69/78 | (2006.01) | |
| C07C 271/44 | (2006.01) | |
| C07C 69/28 | (2006.01) | |
| C07D 265/30 | (2006.01) | |
| C07C 271/56 | (2006.01) | |
| A61K 31/222 | (2006.01) | |
| C07C 69/16 | (2006.01) | |
| A61P 37/04 | (2006.01) | |

(Continued)

(52) U.S. Cl.
CPC ............ *A61K 31/325* (2013.01); *A61K 31/09* (2013.01); *A61K 31/135* (2013.01); *A61K 31/222* (2013.01); *A61K 31/23* (2013.01); *A61P 35/04* (2018.01); *A61P 37/04* (2018.01); *C07C 69/16* (2013.01); *C07C 69/28* (2013.01); *C07C 69/78* (2013.01); *C07C 271/44* (2013.01); *C07C 271/56* (2013.01); *C07D 265/30* (2013.01)

(58) Field of Classification Search
CPC ...... A61K 31/09; A61K 31/23; A61K 31/135; A61K 31/325
USPC ......................................................... 514/490
See application file for complete search history.

(56) References Cited

U.S. PATENT DOCUMENTS

| 4,649,219 A | 3/1987 | Itoh et al. |
| 5,362,615 A | 11/1994 | Hagemann et al. |

(Continued)

FOREIGN PATENT DOCUMENTS

| CN | 1192148 A | 9/1998 |
| DE | 1937384 | * 2/1971 |

(Continued)

OTHER PUBLICATIONS

Dilli et al., Journal of Chromatography (1977), 133(2), 363-6.*

(Continued)

*Primary Examiner* — Niloofar Rahmani
(74) *Attorney, Agent, or Firm* — McCoy Russell LLP

(57) ABSTRACT

Disclosed are hydroquinone compounds, preparation methods therefor, and uses thereof in anti-tumor or immunomodulation. The structural formula of the hydroquinone compounds are shown by formula I,

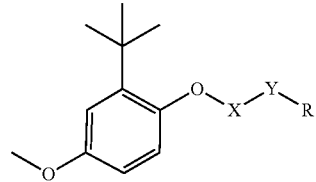

Formula I wherein X is C=O or CH$_2$; Y is NH, O or absent; R is: a substituted or unsubstituted alkyl group having at least one carbon atom, a substituted or unsubstituted cycloalkyl group having at least three carbon atoms, a substituted or unsubstituted alkenyl group or alkynyl group having at least two carbon atoms; and a substituted or unsubstituted aryl group or heteroaryl group containing at least four carbon atoms. The compounds provided slowly release 2-tert-butyl-4-methoxyphenol in vivo and maintain stable plasma concentration of 2-tert-butyl-4-methoxyphenol (T1/2=12-24 h). The compounds provided by the present invention protect the phenolic hydroxyl group of 2-tert-butyl-4-methoxyphenol, avoids environmental oxidation and increase the environmental stability of drugs containing the compounds.

2 Claims, 19 Drawing Sheets

(51) Int. Cl.
   *A61P 35/04*     (2006.01)
   *A61K 31/135*    (2006.01)

(56) References Cited

U.S. PATENT DOCUMENTS

| | | | |
|---|---|---|---|
| 6,127,350 A | 10/2000 | Niesor et al. | |
| 6,403,639 B1 * | 6/2002 | Ishikawa | A61K 31/343 549/462 |

FOREIGN PATENT DOCUMENTS

| | | |
|---|---|---|
| EP | 1308311 A2 | 5/2003 |
| JP | S54147038 A | 11/1979 |
| JP | S5584934 A | 6/1980 |
| JP | H09278741 A | 10/1997 |
| JP | 2009256214 A | 11/2009 |
| RU | 2042659 C1 | 8/1995 |

OTHER PUBLICATIONS

Jha et al., Biochemical Pharmacology (1984), 33(12), 1893-5.*

Shindo et al., Biochemical and Biophysical Research Communications (2013), 436(2), 212-216.*

Wattenberg, L., "Chemoprevention of Cancer," Cancer Research, vol. 45, No. 1, Jan. 1985, 9 pages.

Prochaska, H. et al., "Specificity of Induction of Cancer Protective Enzymes by Analogues of Tert-Butyl-4-Hydroxyanisole (BHA)," Biochemical Pharmacology, vol. 34, No. 21, Nov. 1, 1985, 7 pages.

Chung, F. et al., "Effects of Butylated Hydroxyanisole on the Tumorigenicity and Metabolism of N-Nitrosodimethylamine and N-Nitrosopyrrolidine in A/J Mice," Cancer Research, vol. 46, No. 1, Jan. 1986, 5 pages.

Williams, G. et al., "Safety Assessment of Butylated Hydroxyanisole and Butylated Hydroxytoluene as Antioxidant Food Additives," Food and Chemical Toxicology, vol. 37, No. 9-10, Sep. 1999, 12 pages.

Leclercq, C. et al., "Estimates of the theoretical maximum daily intake of erythorbic acid, gallates, butylated hydroxyanisole (BHA) and butylated hydroxytoluene (BHT) in Italy: a stepwise approach," Food and Chemical Toxicology, vol. 38, No. 12, Dec. 2000, Published Online Oct. 9, 2000, 10 pages.

Mosnacek, J. et al., "New combined phenol/hindered amine photo- and thermal-stabilizers based on toluene-2,4-diisocyanate," Polymer Degradation and Stability, vol. 80, No. 1, Jan. 2003, 14 pages.

Shealy, Y. et al., "Inhibition of Papilloma Formation by Analogues of 7,8-Dihydroretinoic Acid," Journal of Medical Chemistry, vol. 46, No. 10, May 8, 2003, Published Online Apr. 12, 2003, 9 pages.

Murakami, Y. et al., "An ortho dimer of butylated hydroxyanisole inhibits nuclear factor kappa B activation and gene expression of inflammatory cytokines in macrophages stimulated by Porphyromonas gingivalis fimbriae," Archives of Biochemistry and Biophysics, vol. 449, No. 1-2, May 15, 2006, Published Online Mar. 3, 2006, 7 pages.

Soubra, L. et al., "Dietary exposure of children and teenagers to benzoates, sulphites, butylhydroxyanisol (BHA) and butylhydroxytoluen (BHT) in Beirut (Lebanon)," Regulatory Toxicology and Pharmacology, vol. 47, No. 1, Feb. 2007, Published Online Sep. 20, 2006, 10 pages.

Iranpoor, N. et al., "Easily Prepared Azopyridines As Potent and Recyclable Reagents for Facile Esterification Reactions. An Efficient Modified Mitsunobu Reaction," Journal of Organic Chemistry, vol. 73, No. 13, May 31, 2008, 6 pages.

Qian, B. et al., "Macrophage Diversity Enhances Tumor Progression and Metastasis," Cell, vol. 141, No. 1, Apr. 2, 2010, 13 pages.

Zhang, Y. et al., "ROS play a critical role in the differentiation of alternatively activated macrophages and the occurrence of tumor-associated macrophages," Cell Research, vol. 23, No. 7, Jul. 2013, Published Online Jun. 11, 2013, 17 pages.

Shindo, R. et al., "Critical contribution of oxidative stress to TNFα-induced necroptosis downstream of RIPK1 activation," Biochemical and Biophysical Research Communications, vol. 436, No. 2, Jun. 28, 2013, Available Online May 29, 2013, 5 pages.

Phakodee, W. et al., "Ph3P-I2 mediated aryl esterification with a mechanistic insight," Tetrahedron Letters, vol. 57, No. 19, May 11, 2016, 3 pages.

ISA State Intellectual Property Office of the People's Republic of China, International Search Report Issued in Application No. PCT/CN2017/074386, dated May 19, 2017, WIPO, 4 pages.

State Intellectual Property Office of the People's Republic of China, Office Action and Search Report Issued in Application No. 201610037849.5, dated Aug. 23, 2018, 19 pages. (Submitted with Partial Translation).

Russian Federal Institute of Industrial Property, Office Action Issued in Application No. 2018111766/04(018284), dated Oct. 24, 2018, Saint Petersburg, Russia, 17 pages.

Russian Federal Institute of Industrial Property, Office Action Issued in Application No. 2018111766/04(018284), dated Apr. 19, 2019, Saint Petersburg, Russia, 14 pages.

* cited by examiner

 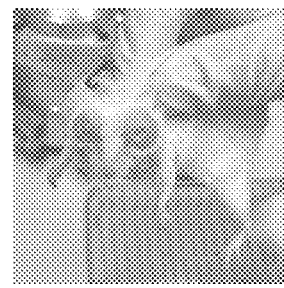
BHA - treated group  
FIG. 1A
Control group  
FIG. 1B
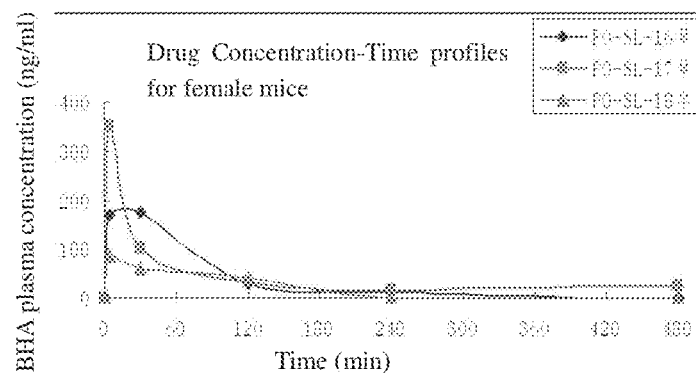
FIG. 2A
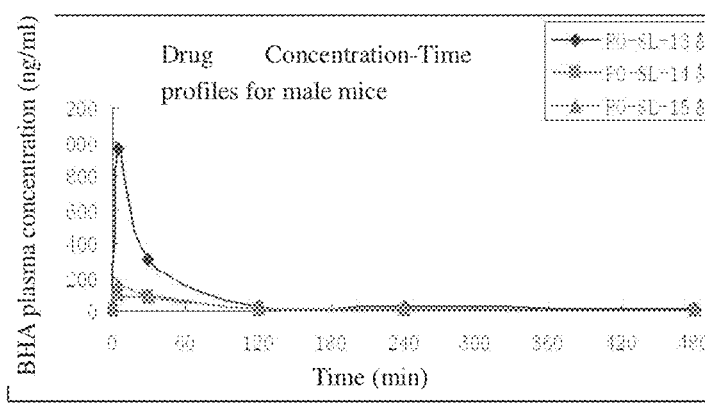
FIG. 2B

HYDROQUINONE COMPOUNDS, PREPARATION METHODS THEREFOR, AND USE IN ANTI-TUMOR OR IMMUNOMODULATION THERAPY

CROSS-REFERENCE TO RELATED APPLICATIONS

The present application is a divisional of U.S. Non-Provisional patent application Ser. No. 16/069,814, entitled "HYDROQUINONE COMPOUNDS, PREPARATION METHODS THEREFOR, AND USE IN ANTI-TUMOR OR IMMUNOMODULATION THERAPY," and filed on Jul. 12, 2018. U.S. Non-Provisional patent application Ser. No. 16/069,814 is a U.S. National Phase of International Patent Application Serial No. PCT/CN2017/074386, entitled "HYDROQUINONE COMPOUND, PREPARATION METHOD THEREFOR, AND APPLICATION IN TUMOUR RESISTANCE OR IMMUNOMODULATION," filed on Feb. 22, 2017. International Patent Application Serial No. PCT/CN2017/074386 claims priority to Chinese Patent Application No. 201610037849.5, filed on Jan. 20, 2016. The entire contents of each of the above-cited applications are hereby incorporated by reference in their entirety for all purposes.

TECHNICAL FIELD

The present invention relates to a series of hydroquinone compounds, preparation methods thereof, and use in anti-tumor or immunomodulation therapy.

BACKGROUND

Solid tumor, in addition to cancer cells, also comprises fibroblast, endothelial cells, various immune cells and a great deal of extracellular matrix, and the like. The immune cells play key roles in the processes of tumor invasion, metastasis and immune escape, wherein tumor-associated macrophages (TAMs) account for considerable proportion in tumor interstitial cells, most of them are migrated and differentiated from peripheral blood monouclear cells, and matured under effect of tumor cells and its microenvironment. TAMs can secrete various growth factors, cytokines, immunosuppressive medium and proteolytic enzyme so as to promote development and metastasis of the tumor.

The TAMs can be polarized into two kinds of phenotypes: M1 macrophage and M2 macrophage. M1 macrophages, also referred as classically activated macrophages, with very strong pro-inflammatory and pathogen killing effect, and can promote Th1 type cell response mediated by inflammatory factors such as IL12, IL23, and the like; M2 macrophages, also referred as non-classically activated macrophages, with functions of immunomodulation, tissue remodeling and pro-angiogenesis, and the like. More and more evidences show that, the TAMs play a key role of "double-edged sword" in the generation and development of malignant tumors: M1 can kill tumor cells, while M2 macrophages play a crucial role in the initiation, promotion, and metastasis of cancer cells (*Cell* 2010, 141:39-51.). The polarization of TAMs is closely related with the tumor microenvironment, and often presents M2 polarized state in malignant tumor. Therefore, redressing the microenvironment of the tumor, by inhibiting the M2 polarization of TAMs, can change the microenvironment of tumor cells, promote death of tumor cells, thereby inhibiting the initiation, promotion, and metastasis of the tumor.

Recent studies have shown that antioxidants such as 2-tert-butyl-4-methoxyphenol (BHA), Apocynin, TEMPO and NAC, and the like can inhibit generation of active oxygen radicals (ROS), thereby inhibit differentiation of monocytes toward M2 macrophages, and then inhibiting the generation of lung cancer in K-ras$^{LA2}$ model mice (Cell Research 2013, 23:898-914.) However, there are also many studies showing that the antioxidants would accelerate the growth of tumor, it is disaccord with the anti-tumor activity in vivo of 2-tert-butyl-4-methoxyphenol, therefore, inhibiting generation of ROS is one factor of inhibiting the M2 polarization of TAMs by 2-tert-butyl-4-methoxyphenol, but not whole, and there are also other mechanisms for inhibiting the M2 polarization of TAMs by BHA, thereby inhibiting generation and development of the tumor (Cancer Res. 1986, 46,165-168; Cancer Res.,1985, 45:1-8.). However, paradoxically, in the early study, there are evidences showing that 2-tert-butyl-4-methoxyphenol has carcinogenic effect (Archives of Biochemistry and Biophysics 2006, 449, 171-177; Regulatory Toxicology and Pharmacology 47 (2007) 68-77; Food and Chemical Toxicology 2000, 38, 1075-1084).

In the literature (Cell Research 2013, 23:898-914.), a fodder of 0.75% BHA is dosed, and the generation of lung cancer was completely inhibited in K-ras$^{LA2}$ model mice. However, according to differences of body surface area and species, this dosage is 7.5 g/day as converting to dosage of a person with 60 kg weight. This dosage substantially exceeds intaking amount of 0.5 mg/kg body weight per day as regulated in European Union and USA, and also exceeds upper limit of 0.2 g/kg of 2-tert-butyl-4-methoxyphenol added in food as regulated in China. Therefore, 2-tert-butyl-4-methoxyphenol cannot become a directly useable tumor therapeutic drug.

Therefore, there is a need to further evaluate tumor therapeutic effects of 2-tert-butyl-4-methoxyphenol.

SUMMARY OF INVENTION

The purpose of the present invention is to provide a series of hydroquinone compounds, preparation methods thereof, and use thereof in anti-tumor or immunomodulation.

The structural formula of the hydroquinone compound provided by the present invention is as shown by formula I, and the pharmaceutically acceptable salts, hydrates or solvates thereof are also in the range to be protected by the present invention,

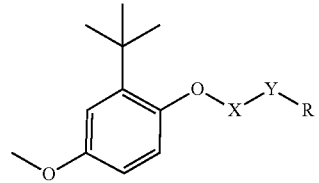

formula I in formula I, X is C=O or CH$_2$, R is selected from any one of the following groups: a substituted or unsubstituted alkyl group having at least one carbon atom, a substituted or unsubstituted cycloalkyl group containing at least three carbon atoms, a substituted or unsubstituted alkenyl group or alkynyl group having at least two carbon atoms, and a substituted or unsubstituted aryl group or heteroaryl group;

in formula I, Y is NH, O or absent;

the substituent groups in R are halogen, amino group, nitrogroup, estergroup, carbonylgroup, amino acid derivatives, natural flavone, naturalalkaloid, polyethyleneglycol, polyglutamic acid or polysaccharide.

In formula I, the number of carbon atoms of the alkyl group is 1~40, preferably 1~30, more preferably 1~25; the number of carbon atoms of the cycloalkyl group may be 3~40, preferably 3~30, more preferably 3~25; the number of carbon atoms of the alkenyl group or alkynyl group may be 2~40, preferably 2~30, more preferably 2~25.

In formula I, the aryl group or heteroaryl group particularly may be naphthalene rings, indole, benzene rings, pyridine, purine, pyrimidine, imidazole, furan, pyrrole or benzoheterocycle, and the like.

In formula I, X and Y are selected from any one of the following 1)~3):
1) when X is C=O, Y is NH;
2) when X is $CH_2$, Y is O;
3) when X is C=O or $CH_2$, Y is absent.

The compound as shown by formula I includes but not limited to any one of the following compounds 1)~66):

1)(2-tert-butyl-4-methoxyphenol) (N-benzyl)carbamate, 2)(2-tert-butyl-4-methoxyphenol) (N-n-butyl)carbamate, 3)(2-tert-butyl-4-methoxyphenol) (N-isopropyl)carbamate, 4)(2-tert-butyl-4-methoxyphenol) (N-cyclohexyl)carbamate, 5)(2-tert-butyl-4-methoxyphenol) (N-phenethyl)carbamate, 6)pivaloyl(2-tert-butyl-4-methoxyphenol-oxyl) methyl ester; 7)2-tert-butyl-4-methoxyphenol benzoate, 8)2-tert-butyl-4-methoxyphenol acetate, 9)2-tert-butyl-4-methoxyphenol nicotinate, 10)2-tert-butyl-4-methoxyphenol isonicotinate, 11)2-tert-butyl-4-methoxyphenol cyclohexenecarboxyl ate, 12)2-tert-butyl-4-methoxyphenol propionate, 13)2-tert-butyl-4-methoxyphenol acrylate, 14) (2-tert-butyl-4-methoxyphenol) 3,4-dimethoxyphenylacetate, 15)2-tert-butyl-4-methoxyphenol butynoate, 16)bis(2-tert-butyl-4-methoxyphenol) 2,2'-biphenyldicarboxylate, 17)(2-tert-butyl-4-methoxyphenol) 2-chloro-5-trifluoromethylbenzoate, 18)(2-tert-butyl-4-methoxyphenol) 3-fluorophenyl acetate, 19)(2-tert-butyl-4-methoxyphenol) (1H-indole-3-yl)acetate, 20)(2-tert-butyl-4-methoxyphenol) 3-(4-fluorophenyl)-propionate, 21)(2-tert-butyl-4-methoxyphenol) N-tert-butoxycarbonylpiperidine-3-formate, 22)di(2-tert-butyl-4-methoxyphenol) terephthalate, 23)(2-tert-butyl-4-methoxyphenol) 3-(3-nitrophenyl)propionate, 24)(2-tert-butyl-4-methoxyphenol) 4-phenylbenzoate, 25)(2-tert-butyl-4-methoxyphenol) 4-methylpyridine-3-formate, 26)(2-tert-butyl-4-methoxyphenol) 4-methoxypyridine-3-formate, 27)2-tert-butyl-4-methoxyphenol hexadecylate, 28)N-tert-butoxycarbonylglycine(2-tert-butyl-4-methoxyphenol)ester, 29)(2-tert-butyl-4-methoxyphenol) 3-fluoro-4-chlorobenzoate, 30)N-tert-butoxycarbonyltetrahydropyrrole, (2-tert-butyl-4-methoxyphenol) benzoheterocycle-3-formate, 31)(2-tert-butyl-4-methoxyphenol) 3-cyanobenzoate, 32)(2-tert-butyl-4-methoxyphenol) N-tert-butoxycarbonylalaninate, 33)(2-tert-butyl-4-methoxyphenol) 2-naphthoate, 34)di(2-tert-butyl-4-methoxyphenol) malonate, 35)(2-tert-butyl-4-methoxyphenol) 3,6-dichloropyridazine-4-formate, 36)(2-tert-butyl-4-methoxyphenol) 1-methylcyclopropyl formate, 37)(2-tert-butyl-4-methoxyphenol) 2-indoleformate, 38)(2-tert-butyl-4-methoxyphenol) 2-chloro-3-picolinate, 39)(2-tert-butyl-4-methoxyphenol) 2-thiopheneacetate, 40)(2-tert-butyl-4-methoxyphenol) 3-(4-methylphenyl)-propionate, 41)(2-tert-butyl-4-methoxyphenol) propiolate, 42)(2-tert-butyl-4-methoxyphenol) 2-phenyl propionate, 43)(2-tert-butyl-4-methoxyphenol) 2-fluoropropionate, 44)(2-tert-butyl-4-methoxyphenol) cyclohexyl acetate, 45)(2-tert-butyl-4-methoxyphenol) cyclopentanecarboxylate, 46)(2-tert-butyl-4-methoxyphenol) adamantaneacetate, 47)(2-tert-butyl-4-methoxyphenol) cyclopropylacetate, 48)(2-tert-butyl-4-methoxyphenol) N-tert-butoxycarbonylpiperidine-4-formate, 49)(2-tert-butyl-4-methoxyphenol) octanoate, 50)(2-tert-butyl-4-methoxyphenol) 7-oxooctanoate, 51)(2-tert-butyl-4-methoxyphenol) cyclohexene-2-carboxylate, 52)(2-tert-butyl-4-methoxyphenol) 2,4,5-trifluorophenylacetate, 53)(2-tert-butyl-4-methoxyphenol) 2-bromo-5-iodo benzoate, 54)(2-tert-butyl-4-methoxyphenol) 2-fluoro-4-nitryl benzoate, 55)(2-tert-butyl-4-methoxyphenol) N-tert-butoxycarbonylpiperidine-3-formate, 56)di(2-tert-butyl-4-methoxyphenol) p-phenylenediacetate, 57)(2-tert-butyl-4-methoxyphenol) 4-benzoyl butyrate, 58)(2-tert-butyl-4-methoxyphenol) 3,5-dimethoxy phenylpropenoate, 59)(2-tert-butyl-4-methoxyphenol) 4-chloropyridine-2-formate, 60)(2-tert-butyl-4-methoxyphenol) N-methylpiperidine-3-formate, 61)(2-tert-butyl-4-methoxyphenol) N-tert-butoxycarbonyl-6-amino pentanoate, 62)(2-tert-butyl-4-methoxyphenol) 3,3,3-trifluoropropionate, 63)(2-tert-butyl-4-methoxyphenol) morpholin-4-yl acetate, 64)(2-tert-butyl-4-methoxyphenol) 3-(3,5-di-tert-butyl-4-hydroxy-phenyl) propionate, 65)di(2-tert-butyl-4-methoxyphenol) adipate; and 66)2-(2-tert-butyl-4-methoxyphenoxy) ethyl acetate.

The present invention further provides a method of preparing the compound as shown by formula I, comprising the following steps (1), (2), (3) or (4):

(1) when X is C=O, Y is NH, comprising the following steps:
$RNH_2$ reacts with triphosgene to obtain R—N=C=O; the compound as shown by formula I is obtained via condensation reaction of R—N=C=O with 2-tert-butyl-4-methoxyphenol;

formula I

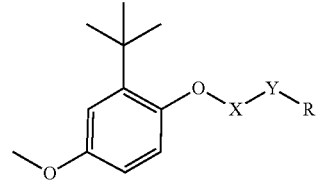

in formula I, $RNH_2$ and R—N=C=O, R is selected from any one of the following groups: a substituted or unsubstituted alkyl group having at least one carbon atom, a substituted or unsubstituted cycloalkyl group having at least three carbon atoms, a substituted or unsubstituted alkenyl group or alkynyl group having at least two carbon atoms and a substituted or unsubstituted aryl group or heteroaryl group;

The substituent groups in R are halogen, amino group, nitro group, ester group, carbonyl group, amino acid derivatives, natural flavone, naturalalkaloid, polyethyleneglycol, polyglutamic acid or polysaccharide;

in formula I, X is C=O, Y is NH;

(2) when X is $CH_2$, Y is O comprising the following steps:
obtaining the compound as shown by formula I via condensation reaction of 2-tert-butyl-4-methoxyphenol sodium with the compound as shown by formula 1;

formula I

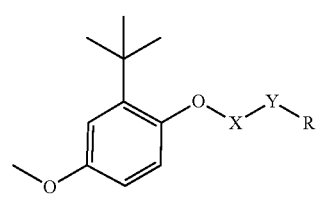

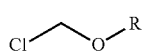

formula 1 in formula I and formula 1, R is selected from any one of the following groups: a substituted or unsubstituted alkyl group having at least one carbon atom, a substituted or unsubstituted cycloalkyl group having at least three carbon atoms, a substituted or unsubstituted alkenyl group or alkynyl group having at least two carbon atoms, and a substituted or unsubstituted aryl group or heteroaryl group;

The substituent groups in R are halogen, amino group, nitrogroup, estergroup, carbonylgroup, amino acid derivatives, natural flavone, natural alkaloid, polyethyleneglycol, polyglutamic acid or polysaccharide;

in formula I, X is CH$_2$, Y is O;

(3) when X is C=O, Y is absent, that is the compound as shown by formula II, comprising the following step 1) or 2):

1) obtaining a compound as shown by formula II via condensation of 2-tert-butyl-4-methoxyphenol sodium with acyl chloride as shown by formula 2;

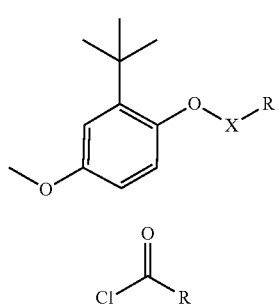

formula II formula 2 in formula II and formula 2, R is selected from any one of the following groups: a substituted or unsubstituted alkyl group having at least one carbon atom, a substituted or unsubstituted cycloalkyl group having at least three carbon atoms, a substituted or unsubstituted alkenyl group or alkynyl group having at least two carbon atoms, and a substituted or unsubstituted aryl group or heteroaryl group;

The substituent groups in R are halogen, amino group, nitrogroup, estergroup, carbonylgroup, amino acid derivatives, natural flavone, natural alkaloid, polyethyleneglycol, polyglutamic acid or polysaccharide;

in formula II, X is C=O;

2) obtaining a compound as shown by formula II via condensation of 2-tert-butyl-4-methoxyphenol sodium with carboxylic acid as shown by formula 3;

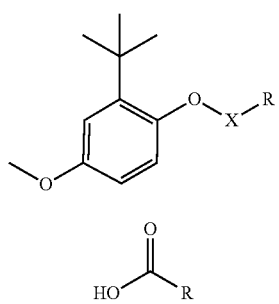

formula II formula 3 in formula II and formula 3, R is selected from any one of the following groups: a substituted or unsubstituted alkyl group having at least one carbon atom, a substituted or unsubstitute dcycloalkyl group having at least three carbon atoms, a substituted or unsubstituted alkenyl group or alkynyl group having at least two carbon atoms, and a substituted or unsubstituted aryl group or heteroaryl group;

The substituent groups in R are halogen, amino group, nitro group, ester group, carbonyl group, amino acid derivatives, natural flavone, natural alkaloid, polyethyleneglycol, polyglutamic acid or polysaccharide;

in formula II, X is C=O;

(4) when X is CH$_2$, Y is absent, that is the compound as shown by formula II, comprising the following step:

obtaining a compound as shown by formula II via condensation reaction of 2-tert-butyl-4-methoxyphenol sodium with a compound as shown by formula 4;

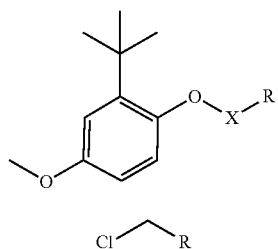

formula II formula 4 in formula II and formula 4, R is selected from any one of the following groups: a substituted or unsubstituted alkyl group having at least one carbon atom, a substituted or unsubstituted cycloalkyl group having at least three carbon atoms, a substituted or unsubstituted alkenyl group or alkynyl group having at least two carbon atoms, and a substituted or unsubstituted aryl group or heteroaryl group;

The substituent groups in R are halogen, amino group, nitro group, ester group, carbonyl group, amino acid derivatives, natural flavone, natural alkaloid, polyethyleneglycol, polyglutamic acid or polysaccharide;

X is CH$_2$.

In the above preparation method, the condensation reaction can be conducted under the conventional reaction conditions, such as room temperature, heating, reflux or ice-bath, and the like.

The compound as shown by formula I, the pharmaceutically acceptable salts thereof, the hydrates or the solvates thereof may be applied to anti-tumor or immunomodulation, that is, the compound as shown by formula I may be utilized to release 2-tert-butyl-4-methoxyphenol in vivo.

The present invention verified that 2-tert-butyl-4-methoxyphenol (BHA) can inhibit the polarization effect of macrophages M2, and verified the anti-tumor metastasis effect of 2-tert-butyl-4-methoxyphenol in the mice model with HER2 breast cancer; dosing in portions the 2-tert-butyl-4-methoxyphenol dosage (50-1000 mg/kg BW) to the HER2 mice model shows obvious anti-tumor effects.

DESCRIPTION OF FIGURES

FIGS. 1A and B are images illustrating that 2-tert-butyl-4-methoxyphenol inhibits the polarization effect of macrophages M2.

FIGS. 2A and B shows the experimental results for metabolism of BHA in the mice in vivo.

FIG. 3AA is a graph illustrating that compound XH2038-5 releases BHA in human plasma.

FIG. 3BB is a graph illustrating that compound XH2039-1 releases BHA in human plasma.

FIG. 3CC is a graph illustrating that compound XH2039-2 releases BHA in human plasma.

FIG. 3DD is a graph illustrating that compound XH2039-3 releases BHA in human plasma.

FIG. 3EE is a graph illustrating that compound XH2039-4 releases BHA in human plasma.

FIG. 3FF is a graph illustrating that compound XH2039-5 releases BHA in human plasma.

FIG. 3GG is a graph illustrating that compound XH2039-6 releases BHA in human plasma.

FIG. 3HH is a graph illustrating that compound XH2040-1 releases BHA in human plasma.

FIG. 3II is a graph illustrating that compound XH2040-2 releases BHA in human plasma.

FIG. 3JJ is a graph illustrating that compound XH2040-4 releases BHA in human plasma.

FIG. 3KK is a graph illustrating that compound XH2040-5 releases BHA in human plasma.

FIG. 3LL is a graph illustrating that compound XH2041-2 releases BHA in human plasma.

FIG. 3MM is a graph illustrating that compound XH2041-3 releases BHA in human plasma.

FIG. 3NN is a graph illustrating that compound XH2041-4 releases BHA in human plasma.

FIG. 3OO is a graph illustrating that compound XH2041-5 releases BHA in human plasma.

FIG. 3PP is a graph illustrating that compound XH2042 releases BHA in human plasma.

FIG. 3QQ is a graph illustrating that compound XH2043-1 releases BHA in human plasma.

FIG. 3RR is a graph illustrating that compound XH2043-2 releases BHA in human plasma.

FIG. 3SS is a graph illustrating that compound XH2043-3 releases BHA in human plasma.

FIG. 3TT is a graph illustrating that compound XH2043-4 releases BHA in human plasma.

FIG. 3UU is a graph illustrating that compound XH2044-1 releases BHA in human plasma.

FIG. 3VV is a graph illustrating that compound XH2044-2 releases BHA in human plasma.

FIG. 3WW is a graph illustrating that compound XH2045-2 releases BHA in human plasma.

FIG. 3XX is a graph illustrating that compound XH2046-3 releases BHA in human plasma.

DETAILED DESCRIPTION

Figure 3A:
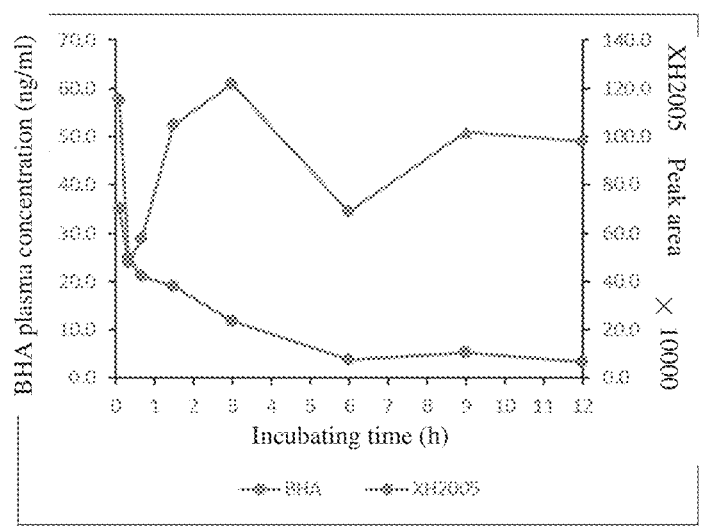
FIG. 3A is a graph illustrating that XH2005 releases BHA in human plasma.
Figure 3B:
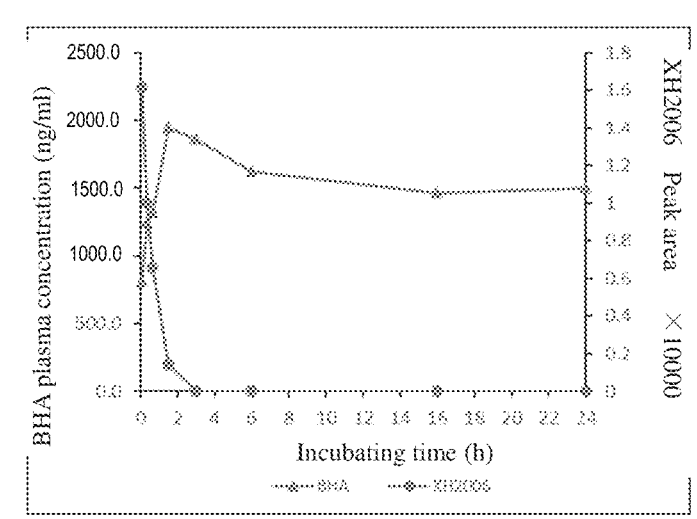
FIG. 3B is a graph illustrating that compound XH2006 releases BHA in human plasma.
Figure 3C:
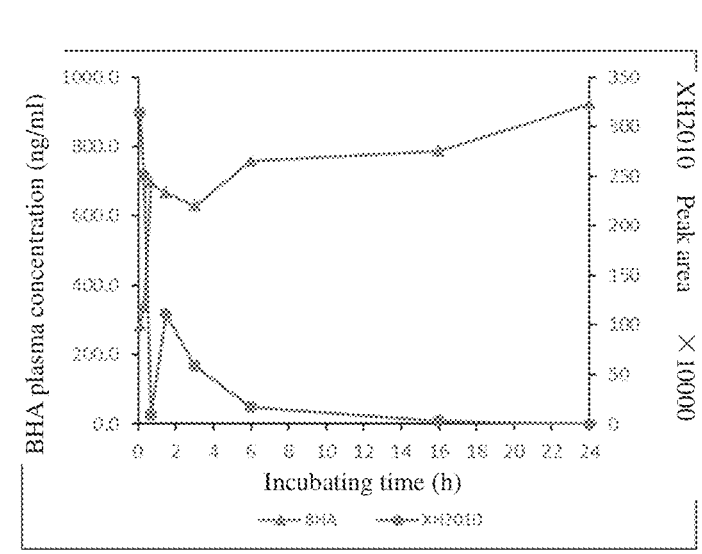
FIG. 3C is a graph illustrating that compound XH2010 releases BHA in human plasma.
Figure 3D:
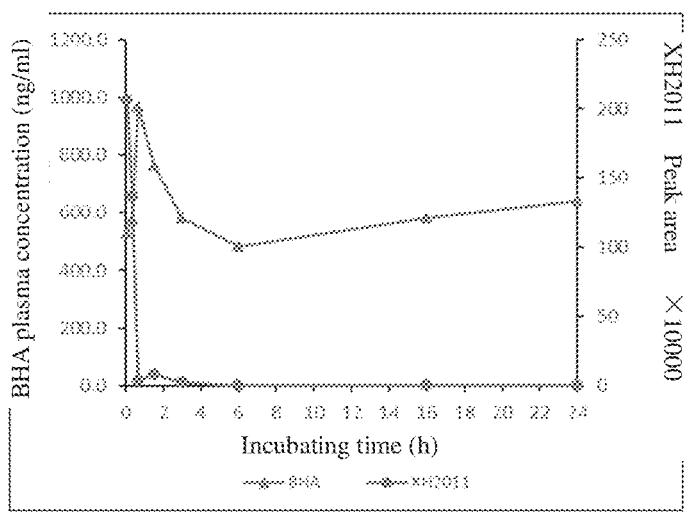
FIG. 3D is a graph illustrating that compound XH2011 releases BHA in human plasma.
Figure 3E:
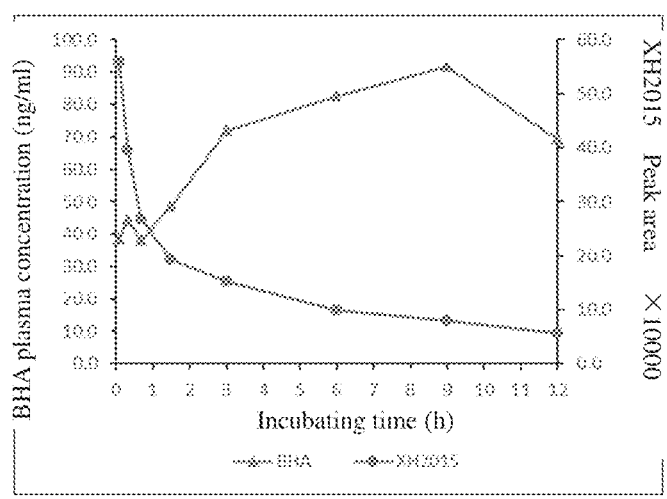
FIG. 3E is a graph illustrating that compound XH2015 releases BHA in human plasma.
Figure 3F:
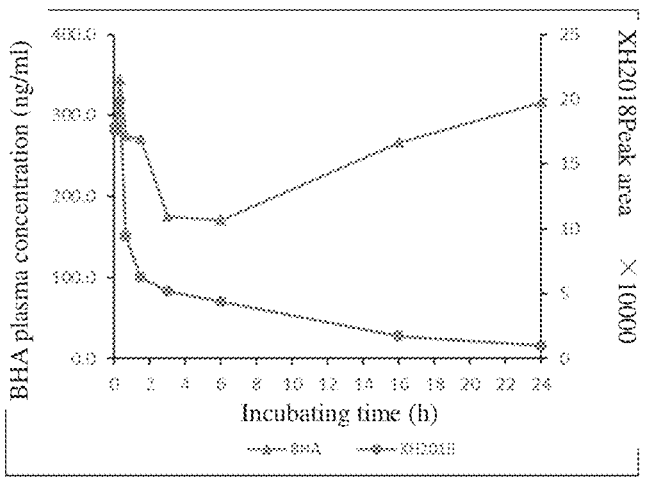
FIG. 3F is a graph illustrating that compound XH2018 releases BHA in human plasma.
Figure 3G:
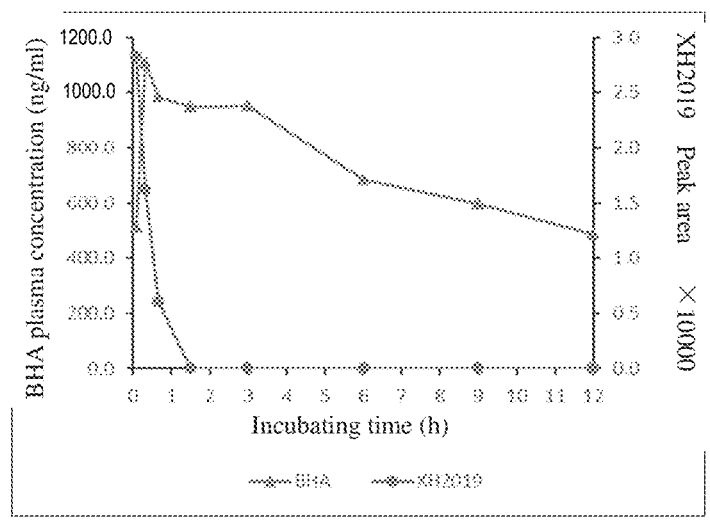
FIG. 3G is a graph illustrating that compound XH2019 releases BHA in human plasma.
Figure 3H:
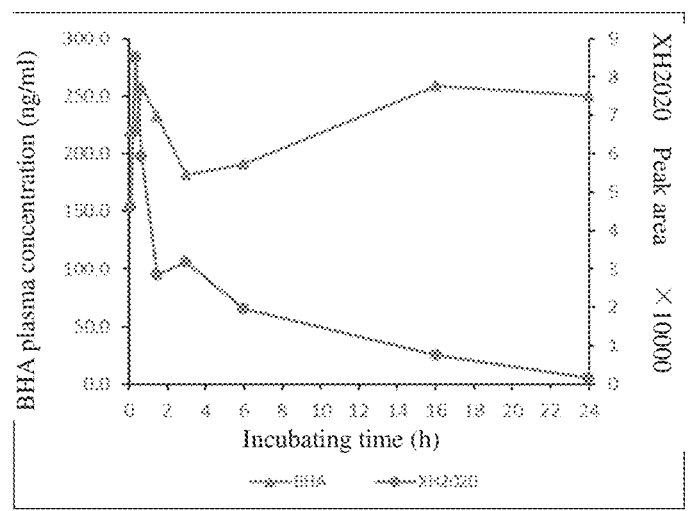
FIG. 3H is a graph illustrating that compound XH2020 releases BHA in human plasma.
Figure 3I:
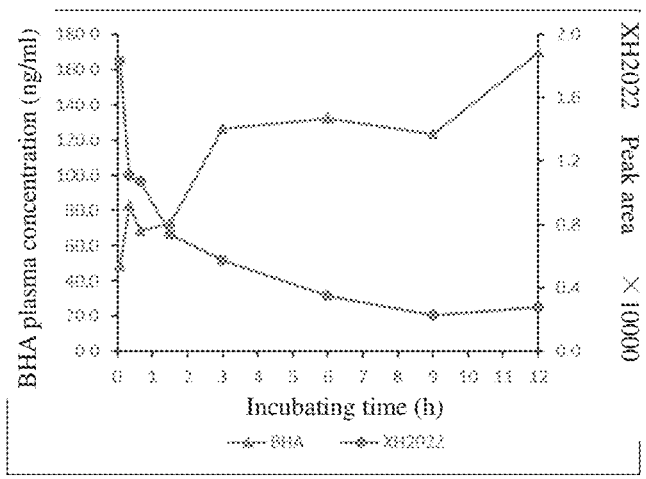
FIG. 3I is a graph illustrating that compound XH2022 releases BHA in human plasma.
Figure 3J:
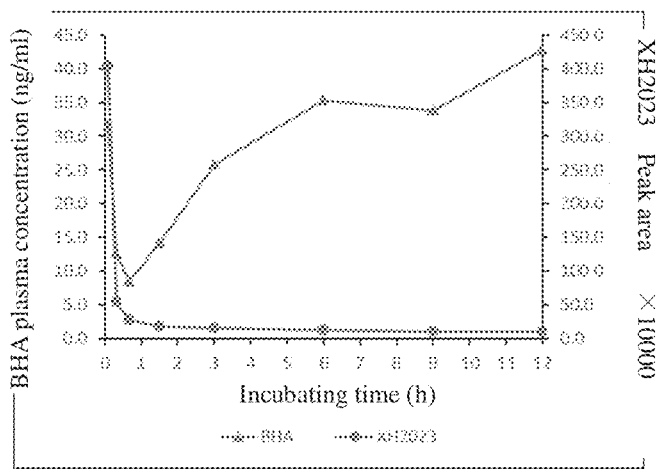
FIG. 3J is a graph illustrating that compound XH2023 releases BHA in human plasma.
Figure 3K:
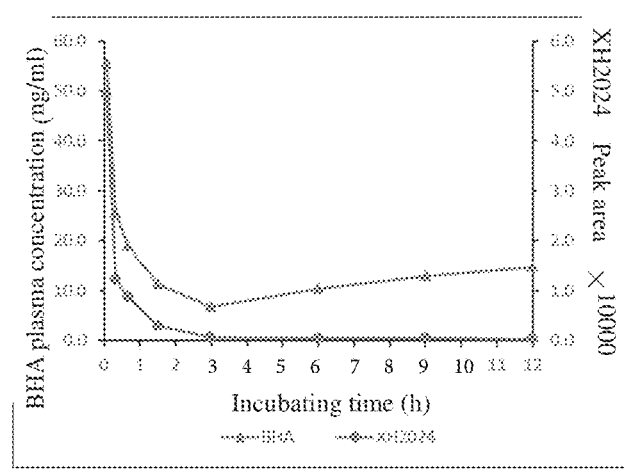
FIG. 3K is a graph illustrating that compound XH2024 releases BHA in human plasma.
Figure 3L:
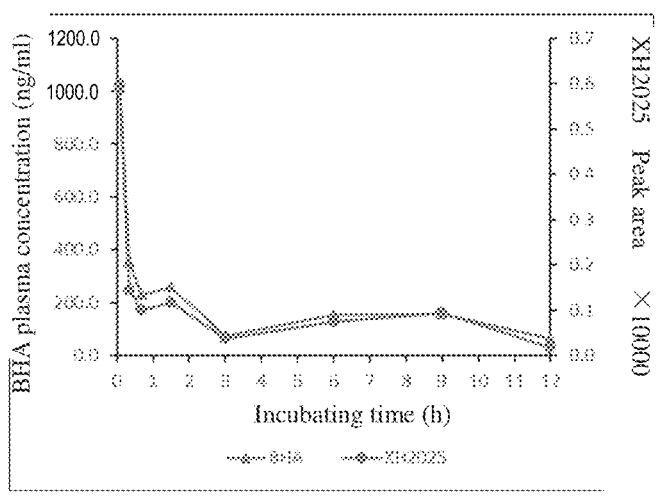
FIG. 3L is a graph illustrating that compound XH2025 releases BHA in human plasma.
Figure 3M:
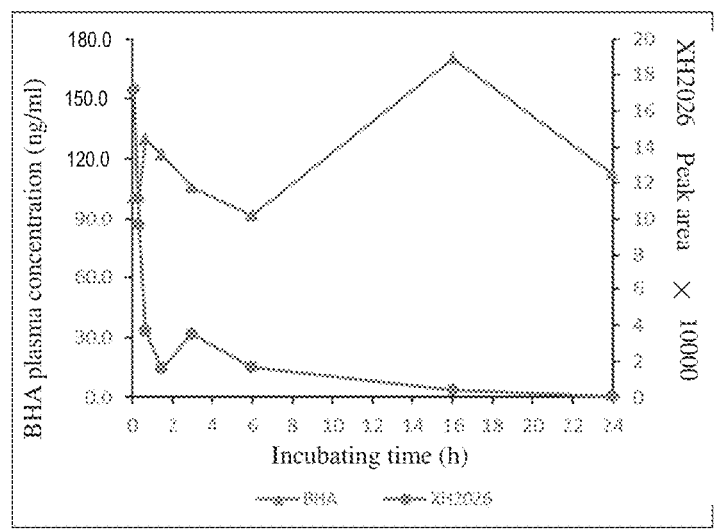
FIG. 3M is a graph illustrating that compound XH2026 releases BHA in human plasma.
Figure 3N:
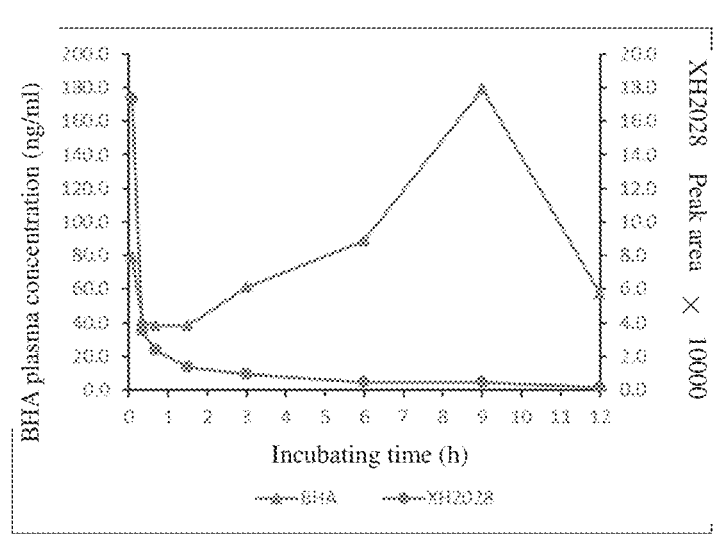
FIG. 3N is a graph illustrating that compound XH 2028 releases BHA in human plasma.
Figure 3O:
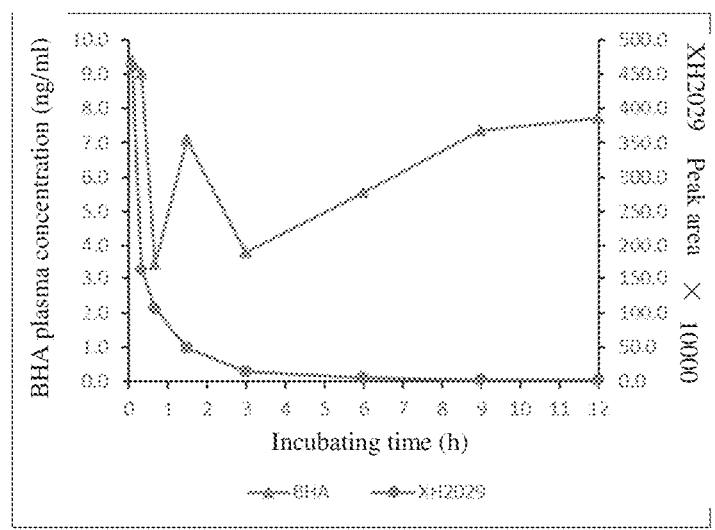
FIG. 3O is a graph illustrating that compound XH2029 releases BHA in human plasma.
Figure 3P:
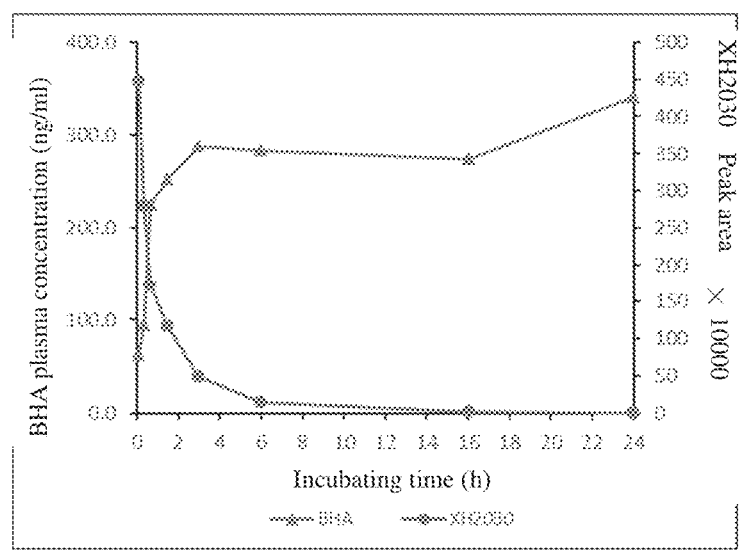
FIG. 3P is a graph illustrating that compound XH2030 releases BHA in human plasma.
Figure 3Q:
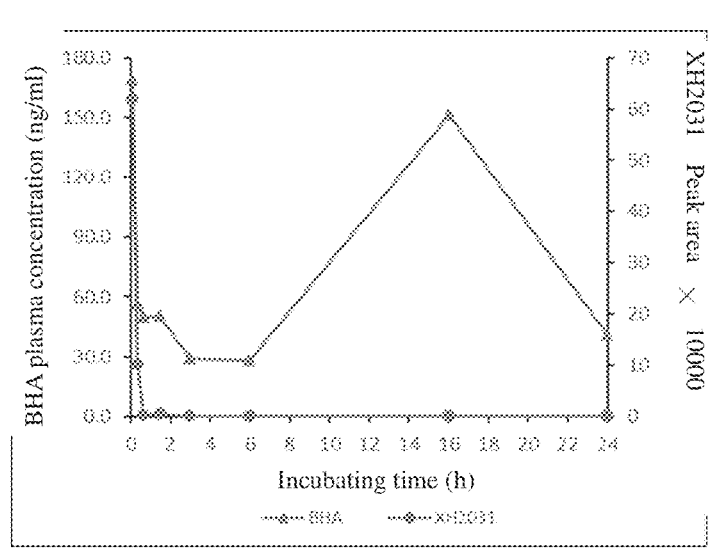
FIG. 3Q is a graph illustrating that compound XH2031 releases BHA in human plasma.
Figure 3R:
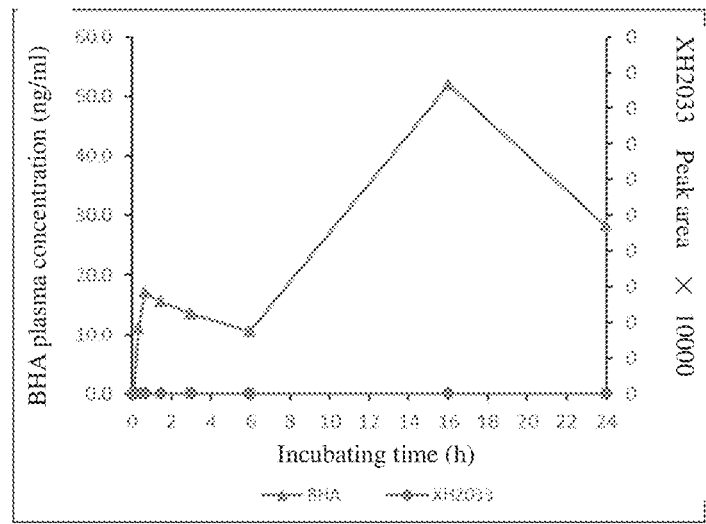
FIG. 3R is a graph illustrating that compound XH2033 releases BHA in human plasma.
Figure 3S:
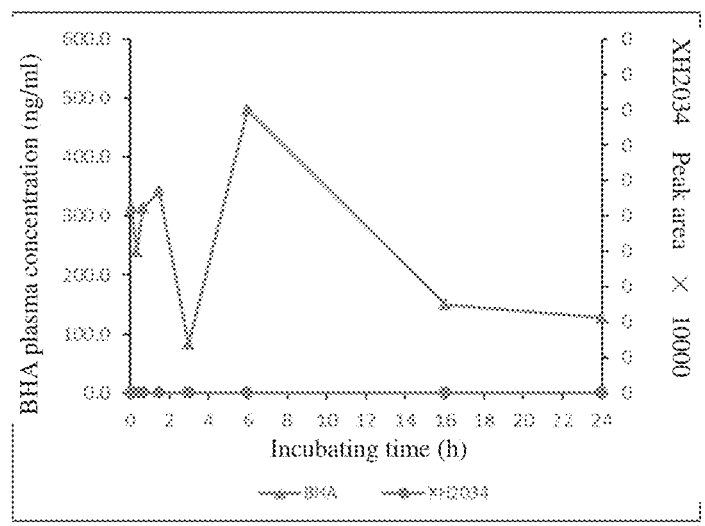
FIG. 3S is a graph illustrating that compound XH2034 releases BHA in human plasma.
Figure 3T:
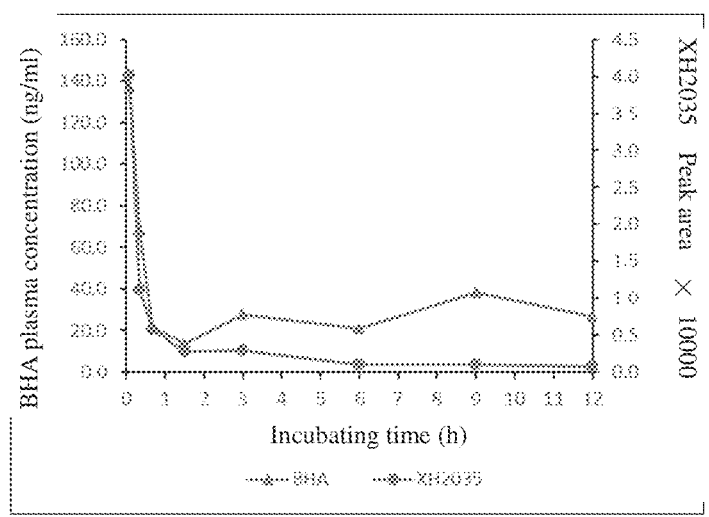
FIG. 3T is a graph illustrating that compound XH2035 releases BHA in human plasma.
Figure 3U:
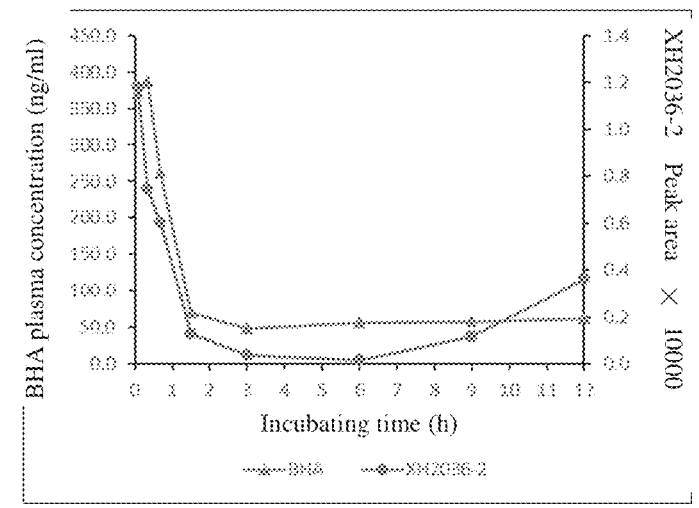
FIG. 3U is a graph illustrating that compound XH2036-2 releases BHA in human plasma.
Figure 3V:
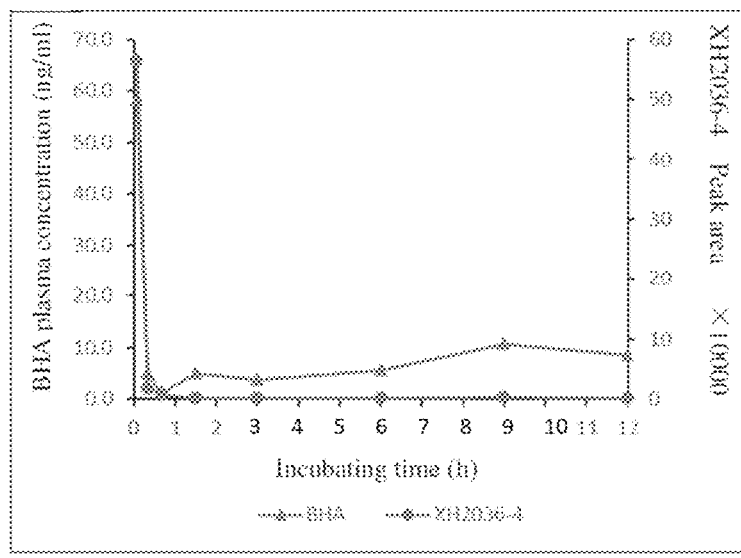
FIG. 3V is a graph illustrating that compound XH2036-4 releases BHA in human plasma.
Figure 3W:
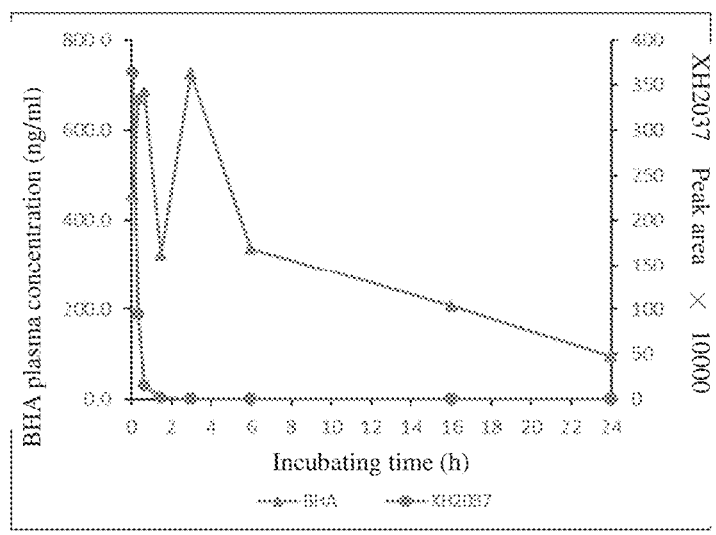
FIG. 3W is a graph illustrating that compound XH2037 releases BHA in human plasma.
Figure 3X:
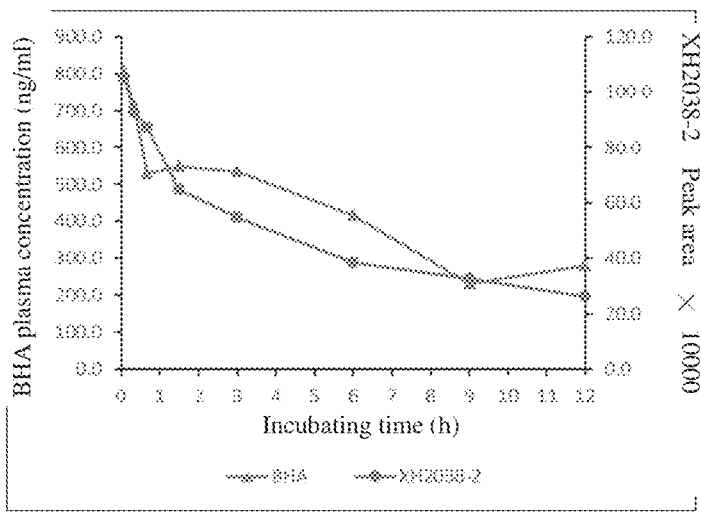
FIG. 3X is a graph illustrating that compound XH2038-2 releases BHA in human plasma.
Figure 3Y:
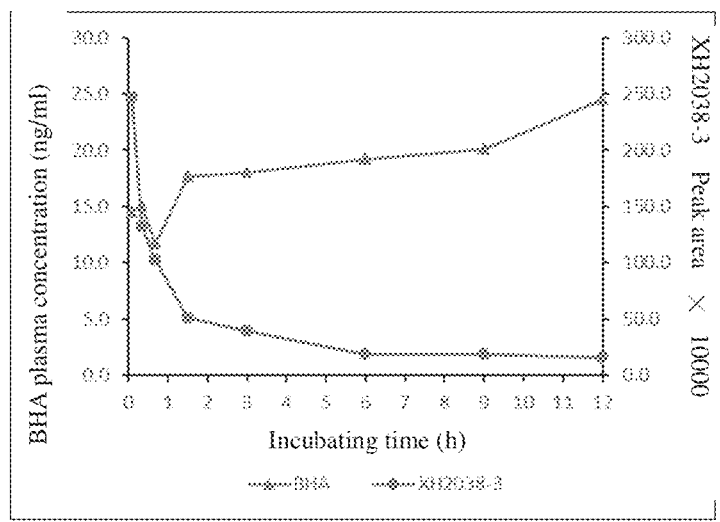
FIG. 3Y is a graph illustrating that compound XH2038-3 releases BHA in human plasma.
Figure 3Z:
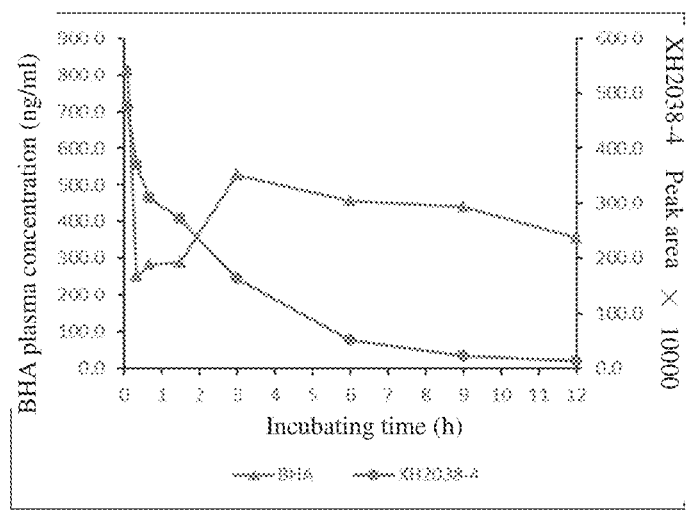
FIG. 3Z is a graph illustrating that compound XH2038-4 releases BHA in human plasma.
Figure 3A:
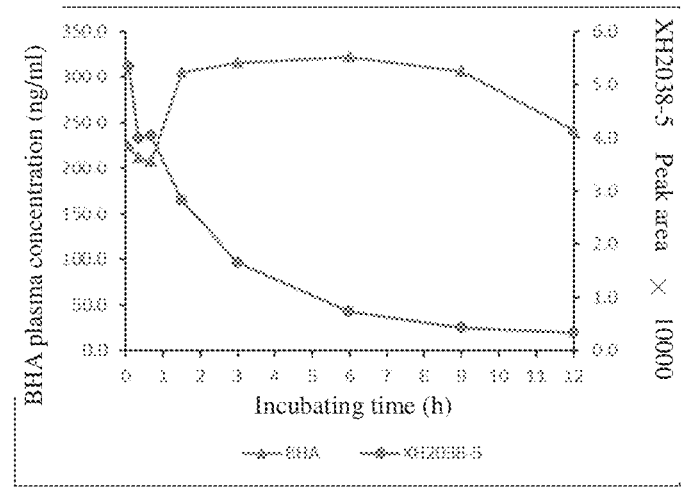
Figure 3B:
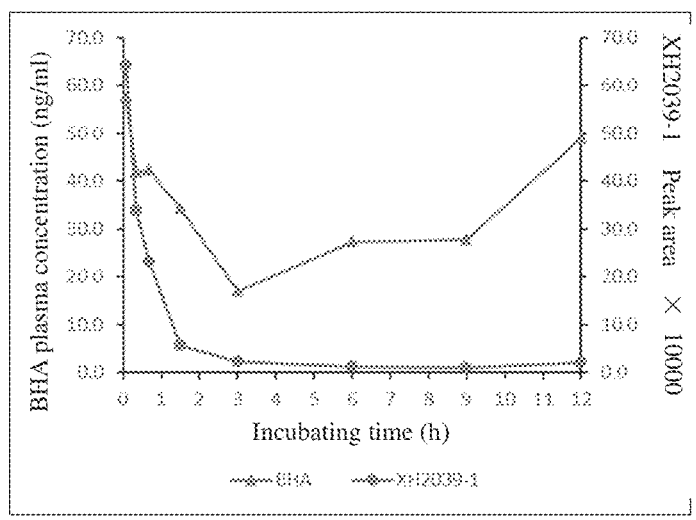
Figure 3C:
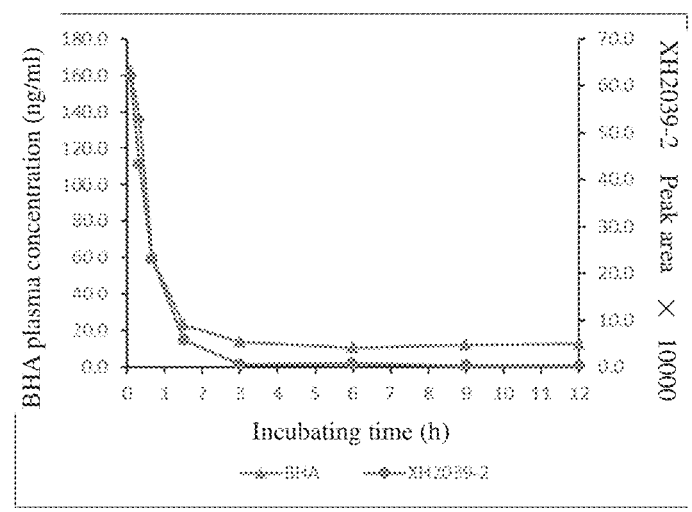
Figure 3D:
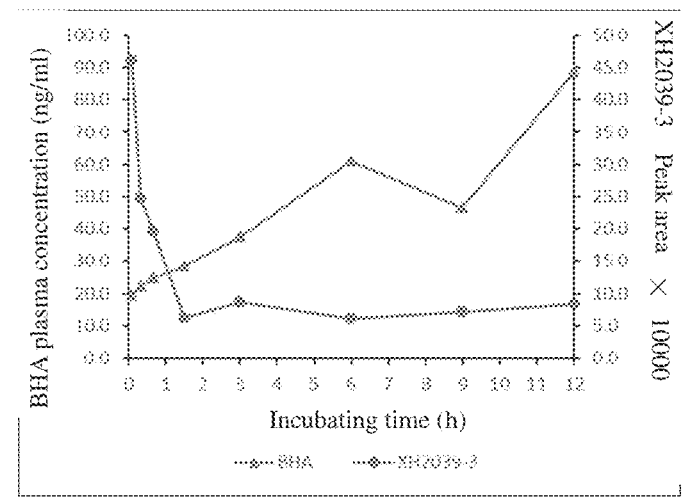
Figure 3E:
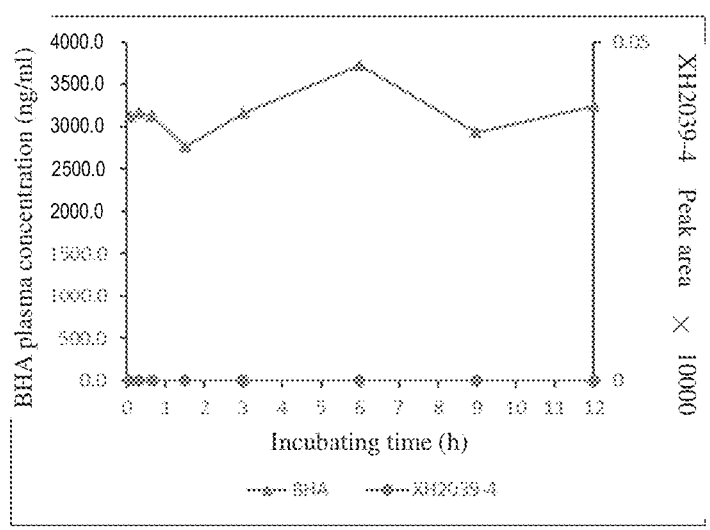
Figure 3F:
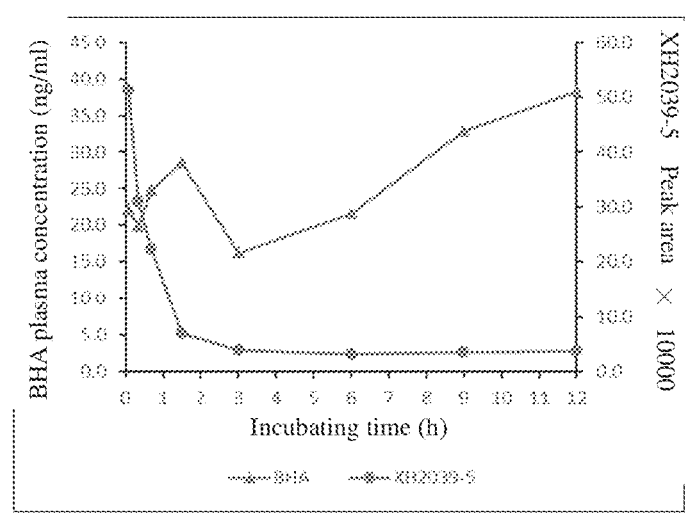
Figure 3G:
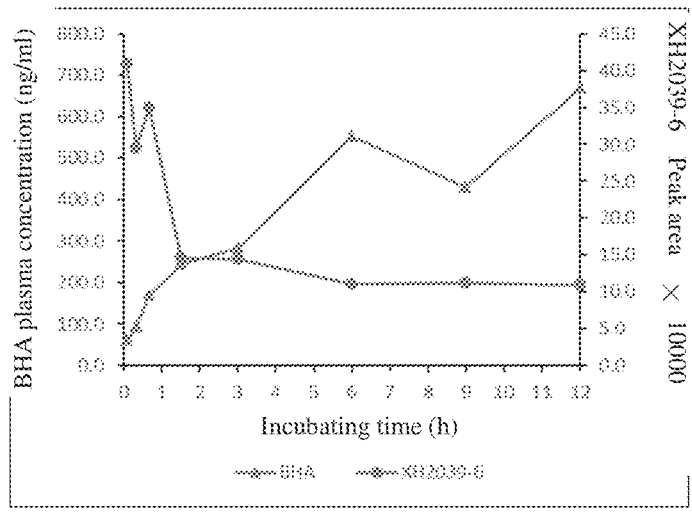
Figure 3H:
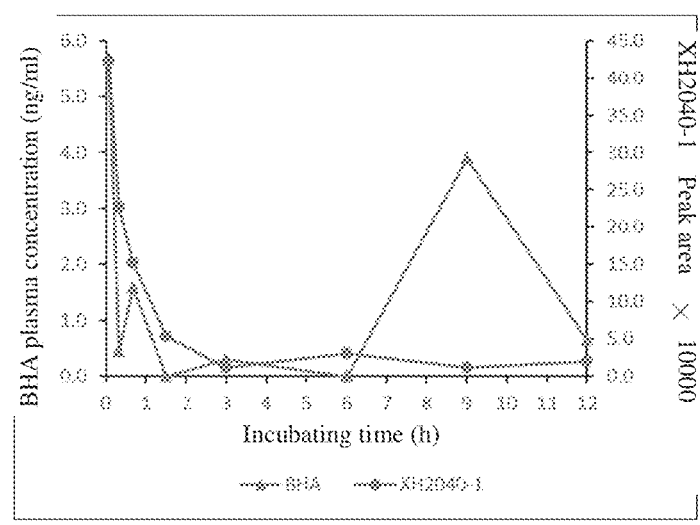
Figure 3I:
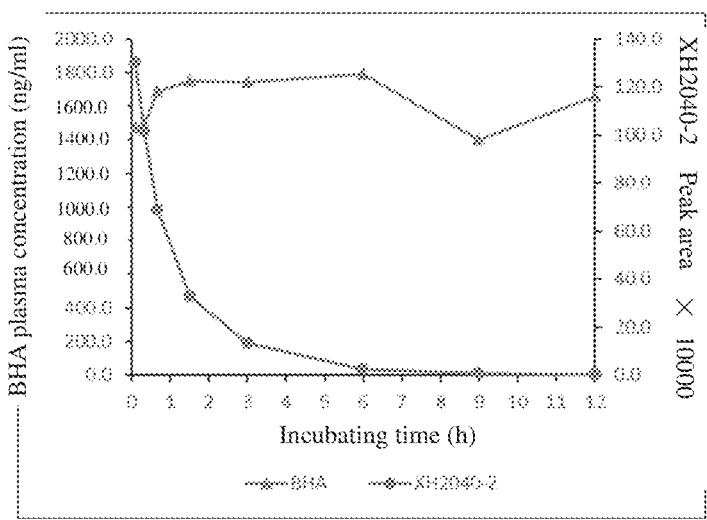
Figure 3J:
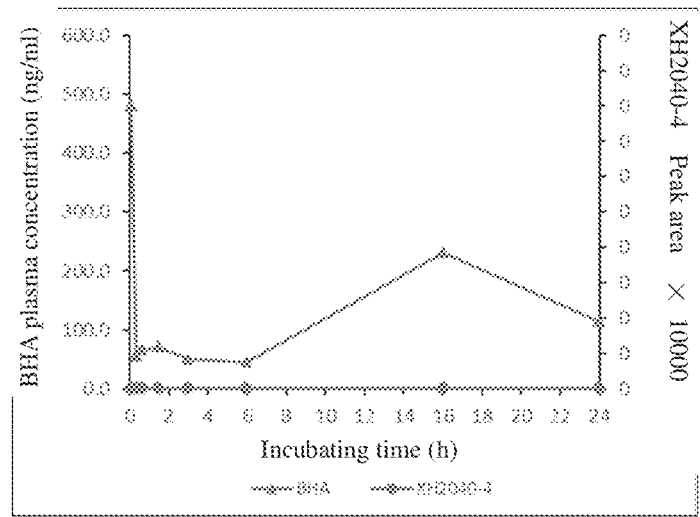
Figure 3K:
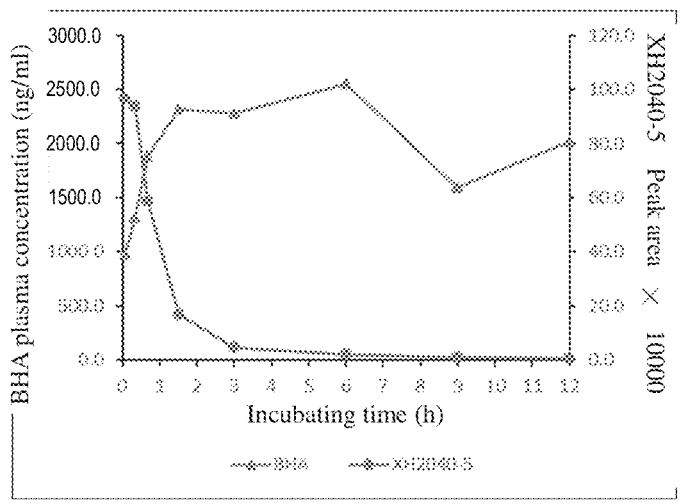
Figure 3L:
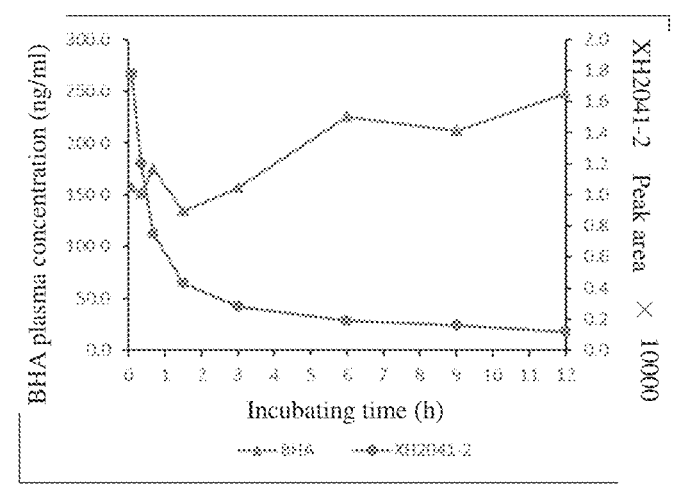
Figure 3M:
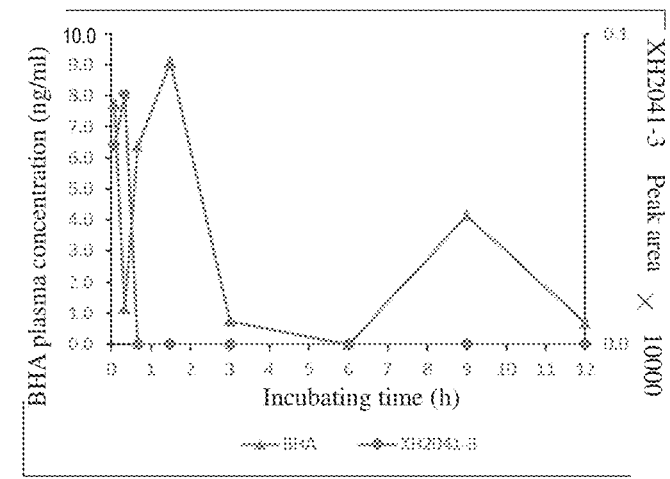
Figure 3N:
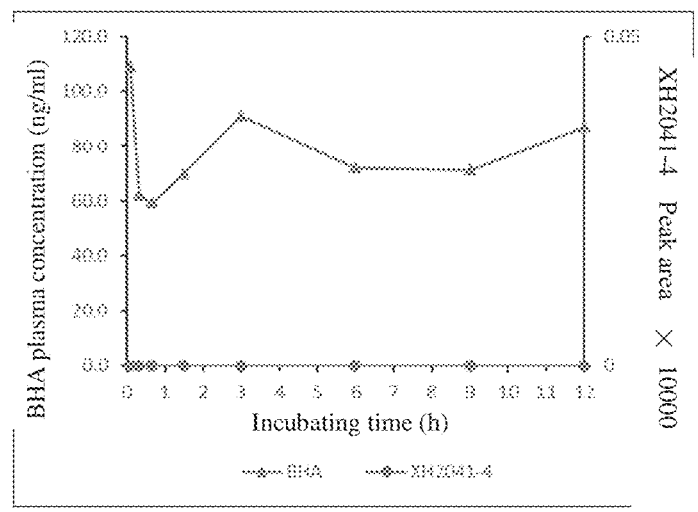
Figure 3O:
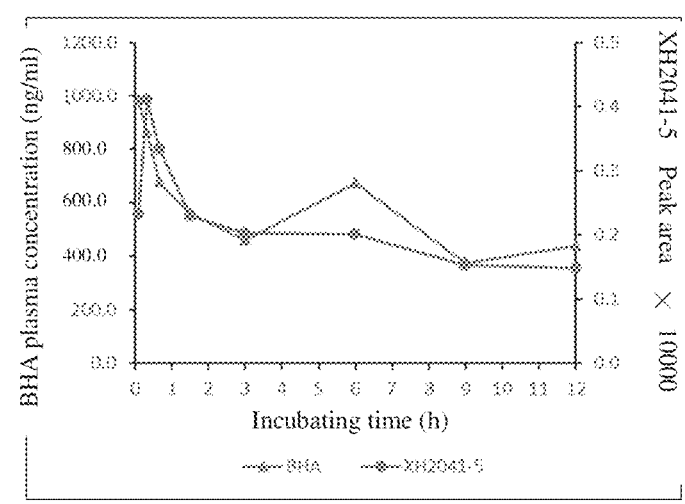
Figure 3P:
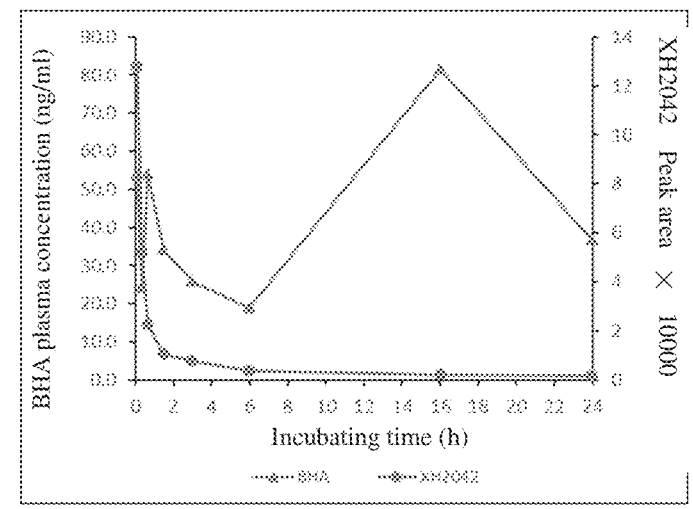
Figure 3Q:
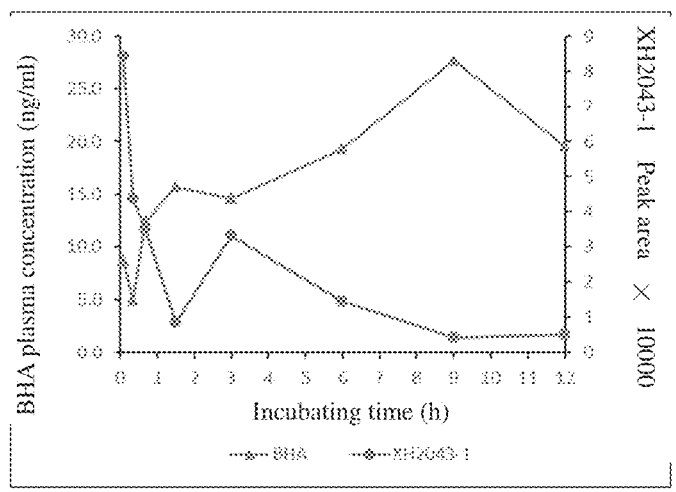
Figure 3R:
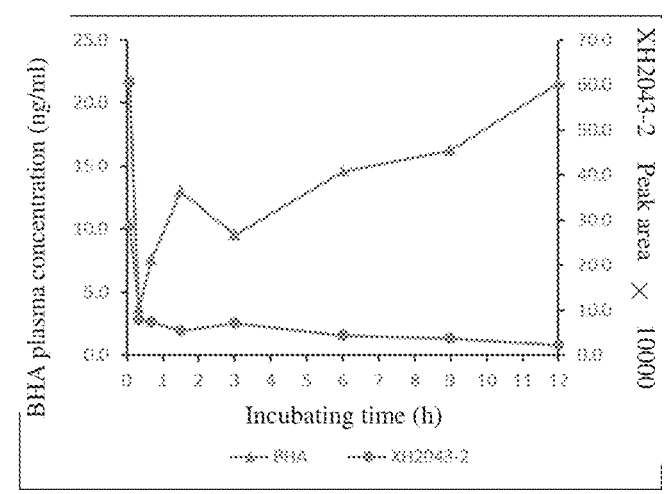
Figure 3S:
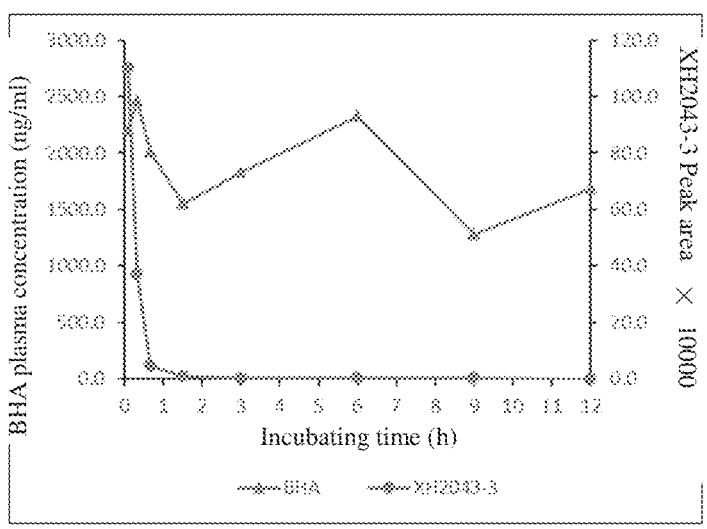
Figure 3T:
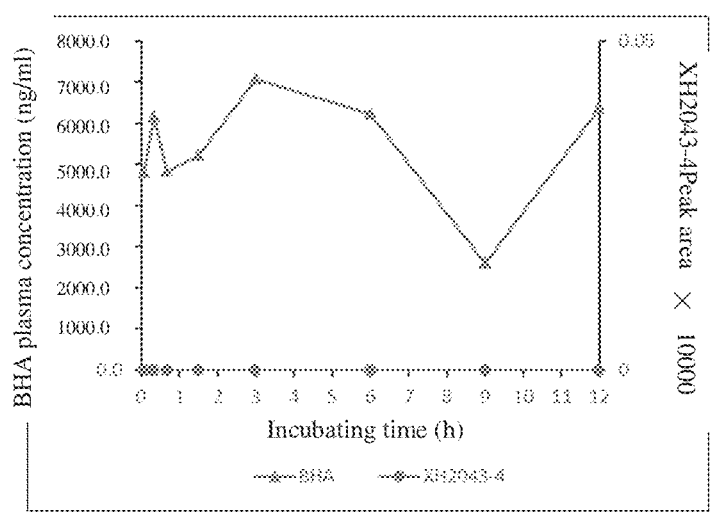
Figure 3U:
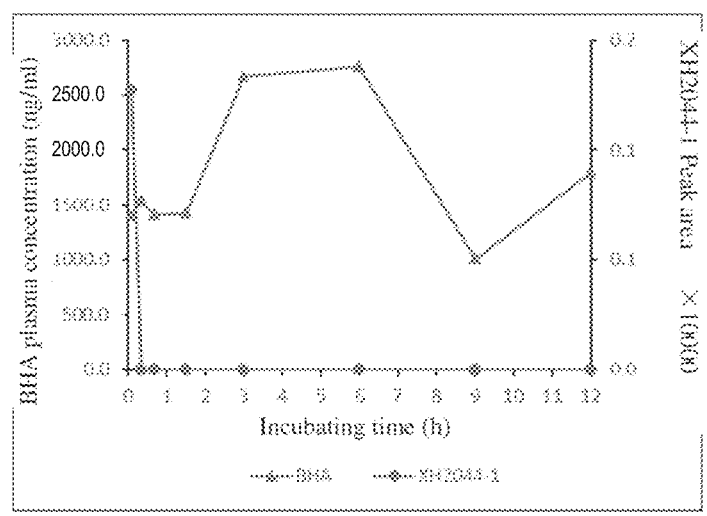
Figure 3V:
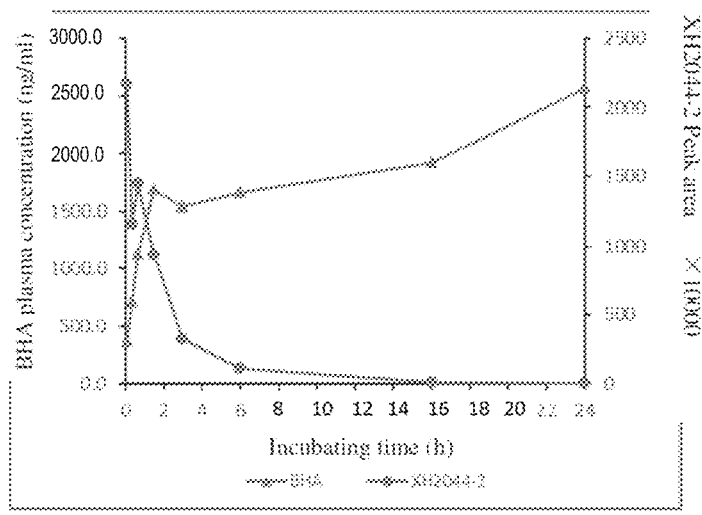
Figure 3W:
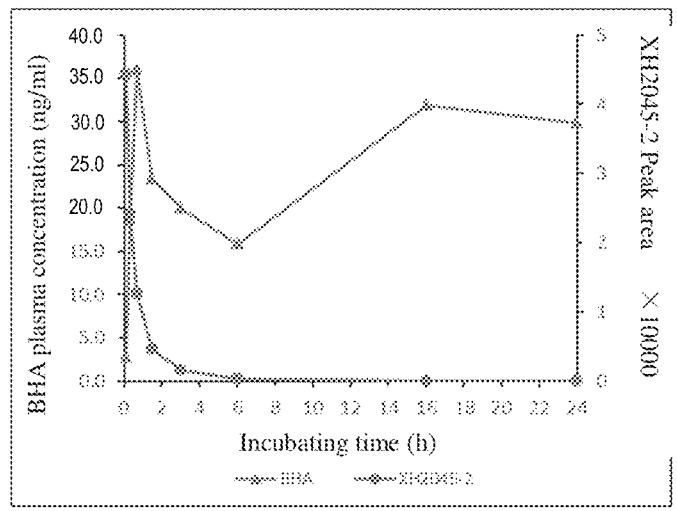
Figure 3X:
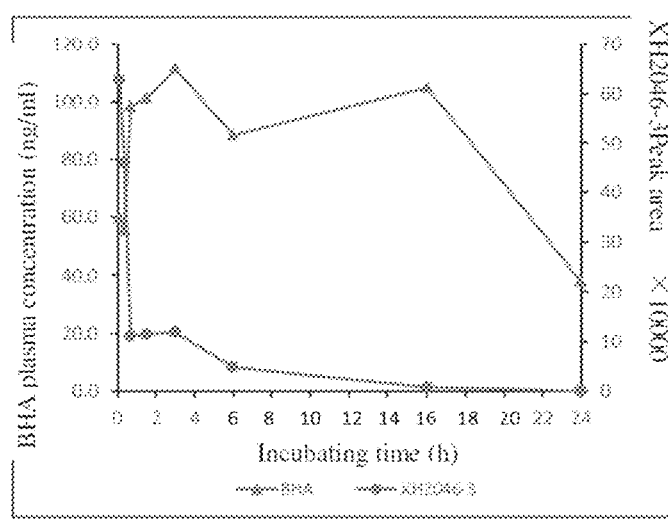

The present invention will be explained through particular examples as follows, however, the present invention is not limited thereto.

All the experimental methods in the following examples are conventional methods, unless otherwise stated; all the regents and materials can be available commercially.

The present invention firstly verified that 2-tert-butyl-4-methoxyphenol (BHA) inhibits the polarization effect of macrophages M2, and verified the anti-tumor metastasis effect of 2-tert-butyl-4-methoxy phenol in the mice model with Her2 breast cancer, as shown by FIG. 1. In the Her2 tumor model with the breast cancer, the metastasis in head is not observed in the BHA treated group (see the left FIG. 1A). The metastasis in head is obvious in mice of the blank control group, leading to blindness (see the right FIG. 1B). At the same time, through drug metabolism tests, it is found that half-life of BHA in vivo is very short, merely 30-60 minutes, as shown by FIGS. 2A and B. Moreover, the present invention conducted a toxicology experiment and found that, merely central effect of partially "hangover" state is seen in the mice dosed with 600 mg/kg, that can recover after half an hour. Half of the mice with 1100 mg/kg are caused to die, and after 30-60 minutes, the symptoms of the toxic reaction in the survival mice are disappear. The toxic effect is not seen in the mice with low dose that is long term dosed for two years. Therefore, in combination with the research results of the metabolic product of 2-tert-butyl-4-methoxyphenol in the literature (having the effect of DNA damage, Food and Chemical Toxicology 1999, 37: 1027-1038), the present invention inferred that the 2-tert-butyl-4-methoxyphenol itself has the effect of anti-tumor, and the action between its metabolic product tert-butylhydroquinone (TBHQ) and DNA may result in its side effects.

It is found by deep analysis that both oral absorption and metabolism of 2-tert-butyl-4-methoxyphenol are very quick (the time to peak is 5 min, the mice $T_{1/2}$=20 min), the plasma concentration for each dosing is a "pulse" with a very small time span, and at the drug concentration peak that is much higher than the minimum effective drug concentration, it is not only disadvantage to the exertion of the therapeutic effect, but also renders unnecessary toxic side effect.

Therefore, if the release of 2-tert-butyl-4-methoxyphenol can be controlled, making it maintain stable plasma concentration, not only can realize the effect of increased effect and decreased toxicity, but also can effectively reduce the dose of 2-tert-butyl-4-methoxyphenol. At the same time, as 2-tert-butyl-4-methoxyphenol is a antioxidant and easily to be oxidized, therefore, the environmental stability and the metabolism in the liver (the first pass effect is serious) are also a immediate obstacle for it to become a drug. In order to control the release of 2-tert-butyl-4-methoxyphenol, increase the environmental stability and reduce the first pass effect as much as possible, increase safety of the drugs, the present invention provides a prodrug 2-tert-butyl-4-methoxyphenol, and verified its release characteristics in vivo and in vitro, the cytotoxicity and the safety in vivo.

EXAMPLE 1

Preparation of 2-tert-butyl-4-methoxyphenol benzoate(XH2005)

2-tert-butyl-4-methoxyphenol (0.9 g, 5 mmol) dissolved in anhydrous tetrahydrofuran (20 mL) is dropwise added to a mixed liquid (10 mL) of sodium hydride (220 mg, 5.5 mmol)/anhydrous tetrahydrofuran at 0-5° C., thereafter, reacting for one hour under the temperature. Benzoyl chloride (0.58 mL, 5 mmol)/dichloromethane (10 mL) is dropwise added to the reaction liquid obtained in the above step, reacting for two hours under the temperature, then reacting for three hours under the room temperature. The solvent is removed under reduced pressure, ethyl acetate (30 mL) and ice water (10 mL) are added to the residue, stirring to clear, separating the liquid and taking the organic layer, washing with water in 10 mL×3, drying with anhydrous sodium sulfate overnight, column chromatograohy (the eluent isethyl acetate:petroleum ether of 4:1) to obtain 1.14 g white solid. Yield is 80%. $^1$H NMR (400 MHz, DMSO-d6) δ: 1.30 (s, 9H), 3.78 (s, 3H), 6.86-6.92 (m, 2H), 7.09-7.11 (d, J=8.4 Hz, 1H), 7.62-7.66 (m, 2H), 7.75-7.79 (m, 1H), 8.15-8.17 (d, J=7.2 Hz, 2H); $^{13}$C NMR (100 MHz, DMSO-d6) δ: 29.8, 34.2, 55.3, 111.1, 113.1, 125.2, 129.2, 129.3, 129.7, 134.1, 141.9, 142.3, 156.6, 165.0.

EXAMPLE 2

Preparation of 2-tert-butyl-4-methoxyphenol acetate (XH2006)

According to the preparation method of Example 1, 2-tert-butyl-4-methoxyphenol reacts with sodium hydride, followed with acetyl chloride to obtain the compound of example 2. Then purify via recrystallization with ethylalcohol. Yield is 90%. $^1$H NMR (400 MHz, CDCl$_3$) δ: 1.33 (s, 9H), 2.32 (s, 3H), 3.79 (s, 3H), 6.72-6.75 (m, 1H), 6.91-6.93 (m, 2H). $^{13}$C NMR (100 MHz, CDCl$_3$) δ: 21.6, 30.1, 34.6, 55.6, 110.6, 113.9, 124.6, 142.4, 142.7, 156.9, 170.2.

EXAMPLE 3

2-tert-butyl-4-methoxyphenol nicotinate (XH2010)

Dissolve niacin (0.62 g, 5 mmol) in dimethylformamide (20 mL), then add dicyclohexylcarbodimide (1200 mg, 6 mmol) and stir for 5 minutes. Add 2-tert-butyl-4-methoxyphenol (900 mg, 5 mmol) and keep the temperature for 35-40° C., overnight. Remove dimethylformamide under reduced pressure. Then dissolve the residue with ethyl acetate (50 mL) and water (2 mL), stir for 20 minutes. The liquid through suction filtration was purified with column chromatography (the eluent is ethyl acetate:petroleum ether=3:1) to obtain the product. The yield is 73%. $^1$H NMR (400 MHz, CDCl$_3$) δ: 1.34 (s, 9H), 3.81 (s, 3H), 6.76-6.81 (m, 1H), 6.97-7.03 (m, 2H), 7.46-7.49 (m, 1H), 8.44-8.47 (dt, J1=8.4 Hz, J2=2.0 Hz, 1H), 8.84-8.86 (dd, J1=4.8 Hz, J2=1.6 Hz, 1H), 9.41-9.42 (d, J=2.0 Hz, 1H); $^{13}$C NMR (100 MHz, CDCl$_3$) δ: 30.2, 34.7, 55.6, 110.8, 114.1, 123.7, 124.7, 125.9, 137.7, 142.5, 142.7, 151.5, 154.1, 157.3, 164.6.

EXAMPLE 4

2-tert-butyl-4-methoxyphenol isonicotinate (XH2011)

The preparation method is the same as that of Example 3, via the condensation reaction of isonicotinic acid and 2-tert-butyl-4-methoxyphenol. Yield is 75%. $^1$H NMR (400 MHz, CDCl$_3$) δ: 1.33 (3,9H), 3.81 (s, 3H), 6.76-6.80 (m, 1H), 6.97-7.01 (m, 2H), 8.00-8.02 (d, J=6.2 Hz, 2H), 8.86-8.87 (d, J=6.2 Hz, 2H). $^{13}$C NMR (100 MHz, CDCl$_3$) δ: 30.4, 34.9, 55.6, 110.8, 114.3, 123.5, 124.5, 137.0, 142.4, 151.0, 157.4, 164.9.

EXAMPLE 5

Preparation of 2-tert-butyl-4-methoxyphenol cyclohexenecarboxylate (XH2015)

The preparation method is the same as that of Example 3. The cyclohexenecarboxylic acid and 2-tert-butyl-4-methoxyphenolester are condensed, and the yield is 75%. $^1$H NMR (400 MHz, CDCl$_3$) δ (ppm): 1.32 (s, 9H), 1.83-1.87 (m, 1H), 2.16-2.23 (m, 3H), 2.43-2.45 (m, 2H), 2.81-2.84 (m, 1H), 3.79 (s, 3H), 5.75 (d, J=1.1 Hz, 2H), 6.71-6.74 (m, 1H), 6.85-6.87 (d, J=8.8 Hz, 1H), 6.92-6.93 (d, J=3.0 Hz, 1H). $^{13}$C NMR (100 MHz, CDCl$_3$) δ (ppm): 24.5, 24.9, 27.4, 30.0, 34.5, 39.9, 55.4, 110.5, 113.7, 124.4, 125.0, 126.8, 142.2, 142.9, 156.7, 174.8.

EXAMPLE 6

2-tert-butyl-4-methoxyphenol propionate (XH2016)

The preparation method is the same as that of Example 3, via the condensation reaction of propionic acid and 2-tert-butyl-4-methoxyphenol, the yield is 85%. $^1$HNMR (400 MHz, CDCl$_3$) δ: 1.27-1.32 (m, 12H), 2.59-2.63 (q, J=3.56 Hz, 2H), 3.79 (s, 3H), 6.77-6.75 (m, 1H), 6.89-6.93 (m, 2H). $^{13}$C NMR (100 MHz, CDCl$_3$) δ (ppm): 9.0, 28.3, 30.1, 34.6, 55.5, 110.5, 113.8, 124.5, 142.3, 142.8, 156.8, 173.4.

EXAMPLE 7

2-tert-butyl-4-methoxyphenol acrylate (XH2017)

The preparation method is the same as that of Example 3, via the condensation reaction of acrylic acid and 2-tert-butyl-4-methoxyphenol, the yield is 55%. $^1$H NMR (400 MHz, CDCl$_3$) δ (ppm): 6.94-6.97 (m, 2H), 6.77-6.75 (m, 1H), 6.60 (m, 1H), 6.36 (m, 1H), 6.03-6.06 (d, J=24 Hz, 1H), 3.81 (s, 3H), 1.33 (s, 9H) $^{13}$C NMR (100 MHz, CDCl$_3$) δ (ppm): 156.8, 142.5, 132.6, 128.5, 124.5, 113.9, 110.5, 55.5, 34.6, 30.0.

EXAMPLE 8

(2-tert-butyl-4-methoxyphenol) 3,4-dimethoxyphenylacetate (XH2018)

The preparation method is the same as that of Example 3, via the condensation reaction of 3,4-dimethoxyphenylacetic acid and 2-tert-butyl-4-methoxyphenol, and the yield is 83%. $^1$H NMR (400 MHz, CDCl$_3$) δ (ppm): 6.92-6.84 (m, 5H), 6.72-6.68 (m, 1H), 3.88 (s, 6H), 3.82(s, 2H), 3.78 (s, 3H), 1.27 (s, 9H). $^{13}$C NMR (100 MHz, CDCl$_3$) δ (ppm): 170.8, 157.0, 149.1, 148.4, 142.9, 142.5, 125.7, 124.5, 122.0, 113.9, 112.7, 111.3, 110.6, 56.1, 56.0, 55.6, 41.8, 34.6, 30.0.

EXAMPLE 9

2-tert-butyl-4-methoxyphenol butynoate (XH2019)

The preparation method is the same as that of Example 3, via the condensation reaction of butynoic acid and 2-tert-butyl-4-methoxyphenol, and the yield is 41%. $^1$H NMR (400 MHz, CDCl$_3$) δ: 1.35 (s, 9H), 2.07 (s, 3H), 3.82 (s, 3H), 6.77-6.75 (m, 1H), 6.94-6.97 (m, 2H). $^{13}$C NMR (100 MHz, CDCl$_3$) δ (ppm): 29.5, 30.2, 34.7, 55.6, 72.6, 88.1, 110.6, 114.0, 124.5, 142.1, 142.7, 153.0, 157.3.

EXAMPLE 10 bis(2-tert-butyl-4-methoxyphenol)2,2'-biphenyldicarboxylate (XH2020)

The preparation method is the same as that of Example 3. 2,2'-biphenyldicarboxylic acid and 2-tert-butyl-4-methoxyphenol are reacted based on the feeding ratio in the molar ratio of 1:2, and the yield is 62%. $^1$H NMR (400 MHz, CDCl$_3$) δ (ppm): 1.26 (s, 9H), 3.76 (s, 6H), 6.65-6.68 (m, 2H), 6.77-6.79 (m, 2H), 6.87-6.88 (m, 2H), 7.26-7.29 (m, 2H), 7.45-7.48 (m, 2H), 7.55-7.58 (m, 2H), 8.19-8.21 (dd, J1=7.8 Hz, J2=1.4 Hz, 2H). $^{13}$C NMR (100 MHz, CDCl$_3$) δ(ppm): 28.8, 33.2, 54.2, 109.2, 112.4, 123.2, 126.2, 127.6, 129.1, 130.7, 141.3, 141.5, 142.8, 155.4, 164.4.

EXAMPLE 11

(2-tert-butyl-4-methoxyphenol) 2-chloro-5-trifluoromethylbenzoate (XH2021)

The preparation method is the same as that of Example 3, via the condensation reaction of 2-chloro-5-trifluoromethylbenzoic acid and 2-tert-butyl-4-methoxyphenol, and yield is 74%. $^1$H NMR (400 MHz, CDCl$_3$) δ (ppm): 1.38 (s, 9H), 3.83 (s, 3H), 6.80-6.82 (m, 1H), 6.99-7.02 (m, 1H), 7.06-7.08 (m, 1H), 7.60-7.64 (m, 1H), 7.74-7.78 (m, 1H), 8.32 (s, 1H), $^{13}$C NMR (100 MHz, CDCl$_3$) δ (ppm): 30.2, 34.7, 55.6, 110.8, 114.1, 124.5, 128.8, 129.7, 130.5, 132.3, 138.5, 142.6, 157.4, 163.5.

EXAMPLE 12

(2-tert-butyl-4-methoxyphenol) 3-fluorophenylacetate (XH2022)

The preparation method is the same as that of Example 3, via the condensation reaction of 3-fluorophenylacetic acid and 2-tert-butyl-4-methoxyphenol, the yield is 80%. $^1$H NMR (400 MHz, CDCl$_3$) δ (ppm): 1.23 (s, 9H), 3.78 (s, 3H), 3.88 (s, 2H), 6.68-6.71 (m, 1H), 6.81-6.85 (m, 2H), 6.90-7.10 (m, 1H), 7.12-7.18 (m, 1H),7.32-7.38 (m, 1H), $^{13}$C NMR (100 MHz, CDCl$_3$) δ (ppm): 29.9, 34.5, 41.7, 55.5, 110.5, 113.8, 114.3, 114.5, 116.6, 124.3, 125.3, 130.1, 130.2, 135.3, 135.4, 142.3, 142.6, 156.9, 161.9, 164.1, 169.8.

EXAMPLE 13

(2-tert-butyl-4-methoxyphenol) (1H-indole-3-yl) acetate (XH2023)

The preparation method is the same as that of Example 3, via the condensation reaction of 1H-indole-3-acetic acid and 2-tert-butyl-4-methoxyphenol, the yield is 65%. $^1$H NMR (400 MHz, CDCl$_3$) δ (ppm): 1.32 (s, 9H), 3.81 (s, 3H), 6.66-6.70 (m, 2H), 6.78-6.82 (m, 1H), 6.85-6.90 (m, 1H), 7.12-7.42 (m, 2H), 7.67 (m, 1H),8.32 (s, 1H), $^{13}$C NMR (100 MHz, CDCl$_3$) δ (ppm): 30.0, 32.1, 34.7, 55.7, 107.9, 110.6, 111.0, 111.5, 113.9, 114.2, 119.0, 119.9, 122.4, 123.6, 124.6, 124.7, 132.5, 143.2, 143.7, 157.0, 157.5, 163.7, 171.2.

EXAMPLE 14

(2-tert-butyl-4-methoxyphenol) 3-(4-fluorophenyl)-propionate (XH2024)

The preparation method is the same as that of Example 3, via the condensation reaction of 3-(4-fluorophenyl)-propionic acid and 2-tert-butyl-4-methoxyphenol, the yield is 64%. $^1$H NMR (400 MHz, CDCl$_3$) δ (ppm): 1.28 (s, 9H), 2.88 (m, 2H), 3.06 (m, 2H), 3.82 (s, 3H), 6.52 (m, 1H), 6.79 (m, 1H), 6.91 (m, 1H), 6.99 (m, 2H),7.25 (m, 2H). $^{13}$C NMR (100 MHz, CDCl$_3$) δ (ppm): 30.0, 34.4, 36.6, 55.4, 110.5, 111.7, 113.7, 115.2, 115.4, 124.4, 129.9, 135.7, 142.2, 142.5, 156.8, 160.3, 162.8, 171.6.

EXAMPLE 15

(2-tert-butyl-4-methoxyphenol) N-tert-butoxycarbonylpiperidine-3-formate (XH2025)

The preparation method is the same as that of Example 3, via the condensation reaction of N-tert-butoxycarbonylpiperidine-3-formic acid and 2-tert-butyl-4-methoxyphenol, the yield is 60%. $^1$H NMR (400 MHz, CDCl$_3$) δ (ppm): 1.32 (s, 9H), 1.47 (s, 9H), 1.76-1.82 (m, 2H), 2.22-2.26 (m, 1H), 2.79 (m, 1H), 2.84-2.88 (m, 1H), 3.16-3.20 (m, 1H), 3.82 (s, 3H), 3.97-4.02 (m, 1H), 4.33-4.36 (m, 1H), 6.68 (m, 1H), 6.83 (m, 1H),6.92 (m, 1H), $^{13}$C NMR (100 MHz, CDCl$_3$) δ

(ppm): 24.4, 27.5, 28.6, 29.7, 30.2, 34.8, 42.1, 55.7, 110.8, 113.9, 124.6, 142.8, 154.8, 157.1, 172.6.

EXAMPLE 16 di(2-tert-butyl-4-methoxyphenol) terephthalate (XH2026)

The preparation method is the same as that of Example 3. p-phthalic acid (5 mmol) and 2-tert-butyl-4-methoxyphenol (10 mmol) are condensed, the yield is 55%. $^1$H NMR (400 MHz, CDCl$_3$) δ (ppm): 1.37 (s, 18H), 3.83 (s, 6H), 6.80-6.83 (m, 2H), 7.00-7.05 (m, 4H), 8.38 (s, 4H), $^{13}$C NMR (100 MHz, CDCl$_3$) δ (ppm): 30.1, 34.6, 55.5, 110.7, 113.9, 124.5, 130.4, 134.1, 142.5, 142.6, 157.1, 164.5.

EXAMPLE 17

(2-tert-butyl-4-methoxyphenol) 3-(3-nitrophenyl) propionate (XH2028)

The preparation method is the same as that of Example 3, via the condensation reaction of 3-(3-nitrophenyl)propionic acid and 2-tert-butyl-4-methoxyphenol, the yield is 70%. $^1$H NMR (400 MHz, CDCl$_3$) δ (ppm): 1.33 (s, 9H), 2.94-2.99 (t, J=7.2 Hz, 2H), 3.14-3.20 (t, J=7.2 Hz, 2H), 3.78 (s, 3H), 6.69-6.73 (m, 1H), 6.80-6.83 (d, J=8.8 Hz, 1H), 6.89-6.90 (d, J=2.1 Hz, 1H), 7.45-7.50 (m, 1H), 7.61-7.64 (m, 1H), 8.08-8.11 (m, 1H), 8.14-8.16 (m, 1H). $^{13}$C NMR (100 MHz, CDCl$_3$) δ (ppm): 30.2, 34.5, 36.0, 55.7, 110.7, 114.1, 121.9, 123.5, 124.6, 129.7, 135.2, 142.3, 142.6, 148.5, 157.1, 171.4.

EXAMPLE 18

(2-tert-butyl-4-methoxyphenol) 4-phenylbenzoate (XH2029)

The preparation method is the same as that of Example 3, via the condensation reaction of 4-phenylbenzoic acid and 2-tert-butyl-4-methoxyphenol, the yield is 80%. $^1$H NMR (400 MHz, CDCl$_3$) δ (ppm): 1.38 (s, 9H), 3.80 (s, 3H), 6.78-6.80 (m, 1H), 6.98-7.04 (m, 2H), 7.18-7.22 (m, 2H), 7.63-7.65 (m, 2H), 7.72-7.74 (m, 2H), 8.28-8.30 (m, 2H). $^{13}$C NMR (100 MHz, CDCl$_3$) δ (ppm): 30.1, 34.6, 55.5, 110.6, 113.8, 124.7, 127.3, 128.3, 128.5, 130.7, 139.8, 142.6, 142.8, 146.3, 156.9, 165.6.

EXAMPLE 19

(2-tert-butyl-4-methoxyphenol) 4-methylpyridine-3-formate (XH2030)

The preparation method is the same as that of Example 3, via the condensation reaction of 4-methylpyridine-3-formic acid and 2-tert-butyl-4-methoxyphenol, the yield is 80%. $^1$H NMR (400 MHz, CDCl$_3$) δ (ppm): 1.38 (s, 9H), 2.68 (s, 3H), 3.82 (s, 3H), 6.78-6.81 (m, 1H), 6.98-6.99 (m, 1H), 7.02-7.04 (m, 1H), 7.33-7.35 (m, 1H), 8.34-8.36 (m, 1H), 9.31-9.32 (d, J=1.68 Hz, 1H), $^{13}$C NMR (100 MHz, CDCl$_3$) δ: 24.9, 30.2, 55.5, 110.7, 114.0, 123.4, 124.7, 138.0, 150.4, 156.4, 157.1, 164.0, 164.7.

EXAMPLE 20

(2-tert-butyl-4-methoxyphenol) 4-methoxypyridine-3-formate (XH2031)

The preparation method is the same as that of Example 3, via the condensation reaction of 4-methoxypyridine-3-formic acid and 2-tert-butyl-4-methoxyphenol, the yield is 75%. Due to ortho-methoxy group, a pair of peaks of the stereoisomers resulted from the chiral plane can be seen in NMR, the proportion of the two stereoisomers is 1:2. $^1$HNMR (400 MHz, CDCl$_3$) δ: 1.33 (s, 9H), 3.81 (s, 3H), 3.82 & 4.00 (s, 3H), 6.76-6.81 (m, 1H), 6.97-7.01 (m, 2H), 7.47-7.48 & 8.04-8.05 (m, 1H), 7.55-7.58 & 7.93-7.95 (m, 1H), 8.35-8.37 & 8.63-8.64 (m,1H). $^{13}$C NMR (100 MHz, CDCl$_3$) δ: 30.0, 34.5, 53.8, 55.3, 110.5, 111.6, 113.8, 115.9, 124.3, 139.9, 142.3, 147.9, 150.8, 152.6, 157.1, 157.3, 163.1, 164.1, 164.8.

EXAMPLE 21

2-tert-butyl-4-methoxyphenol hexadecylate (XH2033)

The preparation method is the same as that of Example 3, via the condensation reaction of hexadecylic acid and 2-tert-butyl-4-methoxyphenol, the yield is 75%. $^1$H NMR (400 MHz, CDCl$_3$) δ (ppm): 0.88 (m, 3H), 1.25-1.33 (m, 34H), 1.71-1.79 (m, 2H), 2.55-2.59 (m, 2H), 3.78 (s, 3H), 6.71-6.74 (m, 1H),6.88-6.93 (m, 2H). $^{13}$C NMR (100 MHz, CDCl$_3$) δ (ppm): 14.3, 22.8, 24.9, 29.3, 29.5, 29.6, 29.7, 29.8, 30.1, 32.0, 34.8, 35.0, 55.5, 110.5, 113.9, 124.6, 142.3, 142.8, 156.8, 172.9.

EXAMPLE 22

N-tert-butoxycarbonylglycine(2-tert-butyl-4-methoxyphenol)ester (XH2034)

The preparation method is the same as that of Example 3, via the condensation reaction of N-tert-butoxycarbonylglycine and 2-tert-butyl-4-methoxyphenol, the yield is 45%. $^1$H NMR (400 MHz, CDCl$_3$) δ (ppm): 1.30 (s, 9H), 1.46 (s, 9H), 3.83 (s, 3H), 4.20 (s, 2H), 5.2 (br s, 1H), 6.71-6.73 (m, 1H),6.92-6.94 (m, 2H), $^{13}$C NMR (100 MHz, CDCl$_3$) δ (ppm): 28.2, 30.0, 34.4, 42.9, 55.4, 80.0, 110.4, 113.8, 124.2, 142.2, 155.5, 156.9, 169.5.

EXAMPLE 23

(2-tert-butyl-4-methoxyphenol) 3-fluoro-4-chlorobenzoate (XH2035)

The preparation method is the same as that of Example 3, via the condensation reaction of 3-fluoro-4-chlorobenzoic acid and 2-tert-butyl-4-methoxyphenol, the yield is 78%. $^1$H NMR (400 MHz, CDCl$_3$) δ (ppm): 1.34 (s, 9H), 3.82 (s, 3H), 6.71-6.73 (m, 1H), 6.98-7.00 (m, 2H), 7.56-7.60 (m, 1H), 7.96-7.97 (m, 2H). $^{13}$C NMR (100 MHz, CDCl$_3$) δ: 30.2, 34.7, 55.6, 110.8, 114.1, 118.4, 124.6, 126.6, 130.4, 131.2, 142.6, 156.9, 157.3, 159.4, 164.1.

EXAMPLE 24

N-tert-butoxycarbonyltetrahydropyrrole, (2-tert-butyl-4-methoxyphenol) benzoheterocycle-3-formate (XH2036-1)

The preparation method is the same as that of Example 3, via the condensation reaction of N-tert-butoxycarbonyltetrahydropyrrole, benzoheterocycle-3-formic acid and 2-tert-butyl-4-methoxyphenol, the yield is 70%. $^1$H NMR (400 MHz, CDCl$_3$) δ (ppm): 1.32 (s, 9H), 1.46 (s, 9H), 2.30-2.32 (m, 2H), 3.28-3.34 (m, 1H), 3.38-3.44 (m, 1H), 3.52-3.58

(m, 1H), 3.72-3.82 (m, 2H), 3.82 (s, 3H), 6.70-6.74 (m, 1H), 6.85-6.88 (m,1H),6.92-6.93 (m, 2H). $^{13}$C NMR (100 MHz, CDCl$_3$) δ (ppm): 28.4, 30.0, 34.5, 43.4, 45.1, 47.8, 55.5, 79.5, 110.5, 113.8, 124.3, 142.1, 142.5, 154.2, 156.9, 172.0.

EXAMPLE 25

(2-tert-butyl-4-methoxyphenol) 3-cyanobenzoate (XH2036-2)

The preparation method is the same as that of Example 3, via the condensation reaction of 3-cyanobenzoic acid and 2-tert-butyl-4-methoxyphenol, the yield is 70%. $^1$H NMR (400 MHz, CDCl$_3$) δ (ppm): 1.35 (s, 9H), 3.82 (s, 3H), 6.78-6.81 (m, 1H), 6.99-7.01 (m, 2H), 7.67-7.71 (t, J=3.84 Hz, 1H), 7.92-7.95 (m, 1H), 8.44-8.47 (m, 2H), 8.50 (s, 1H). $^{13}$C NMR (100 MHz, CDCl$_3$) δ (ppm): 30.1, 34.5, 55.6, 110.7, 113.3, 113.9, 117.7, 124.4, 129.8, 131.1, 133.7, 134.1, 136.5, 142.4, 157.2, 163.9.

EXAMPLE 26

(2-tert-butyl-4-methoxyphenol) N-tert-butoxycarbonylalaninate (XH2036-3)

The preparation method is the same as that of Example 3, via the condensation reaction of N-tert-butoxycarbonylalanine and 2-tert-butyl-4-methoxyphenol, the yield is 37%. $^1$H NMR (400 MHz, CDCl$_3$) 1.32 (s, 9H), 1.40 (s, 9H), 1.43 (d, 2H), 3.73 (s, 3H), 4.61 (m, 1H), 6.99-7.01 (m, 2H), 6.78-6.81 (m, 1H).

EXAMPLE 27

(2-tert-butyl-4-methoxyphenol) 2-naphthoate (XH2036-4)

The preparation method is the same as that of Example 3, via the condensation reaction of 2-naphthoic acid and 2-tert-butyl-4-methoxyphenol, the yield is 77%. $^1$HNMR (400 MHz, CDCl$_3$) δ (ppm): 1.32 (s, 9H), 3.73 (s, 3H), 6.84 (m, 1H), 6.88-6.89 (m, 2H), 7.46-7.49 (m, 3H),7.82-7.85 (m, 4H). $^{13}$C NMR (100 MHz, CDCl$_3$) δ (ppm): 30.0, 34.6, 42.4, 55.5, 110.6, 113.9, 124.5, 126.4, 127.6, 127.8, 128.6, 130.7, 131.7, 133.6, 142.4, 142.9, 157.0, 170.5.

EXAMPLE 28 di(2-tert-butyl-4-methoxyphenol) malonate (XH2037)

The preparation method is the same as that of Example 3, via the condensation reaction of malonicacid (5 mmol) and 2-tert-butyl-4-methoxyphenol (10 mmol), the yield is 70%. $^1$H NMR (400 MHz, CDCl$_3$) δ (ppm): 1.35 (s, 18H), 3.80 (s, 6H), 3.88 (s, 2H), 6.75 (m, 2H), 6.94 (m, 2H),6.99-7.01 (m, 2H). $^{13}$C NMR (100 MHz, CDCl$_3$) δ (ppm): 30.2, 34.7, 42.6, 55.5, 110.8, 114.0, 124.4, 142.5, 142.6, 157.3, 165.4.

EXAMPLE 29

(2-tert-butyl-4-methoxyphenol) 3,6-dichloropyridazine-4-formate (XH2038-1)

The preparation method is the same as that of Example 3, via the condensation reaction of 3,6-dichloropyridazine-4-formic acid and 2-tert-butyl-4-methoxyphenol, the yield is 77%. $^1$H NMR (400 MHz, CDCl$_3$) δ (ppm): 1.36 (s, 9H), 3.82 (s, 3H), 6.76-6.79 (m, 1H), 6.97-7.02 (m, 2H),7.99 (s, 1H). $^{13}$C NMR (100 MHz, CDCl$_3$) δ (ppm): 30.2, 34.7, 55.6, 110.8, 114.1, 124.4, 131.5, 137.8, 138.8, 142.3, 142.6, 157.5, 158.0, 161.4.

EXAMPLE 30

(2-tert-butyl-4-methoxyphenol) 1-methylcyclopropyl formate (XH2038-2)

The preparation method is the same as that of Example 1, by reacting 1-methylcyclopropyl formic acid and sulfoxide chloride, and then via the condensation reaction with 2-tert-butyl-4-methoxyphenol sodium, the yield is 87%. $^1$H NMR (400 MHz, CDCl$_3$) δ (ppm): 0.83-0.85 (m, 2H), 1.33 (s, 9H), 1.40-1.42 (m, 2H), 1.46 (s, 3H), 3.78 (s, 3H), 6.72-6.73 (m, 1H), 6.84-6.87 (m, 1H), 6.90-6.92 (m, 1H), $^{13}$C NMR (100 MHz, CDCl$_3$) δ (ppm): 17.3, 19.1, 19.7, 30.1, 34.6, 55.6, 110.6, 113.7, 124.7, 142.4, 143.2, 156.7, 175.2.

EXAMPLE 31

(2-tert-butyl-4-methoxyphenol) 2-indoleformate (XH2038-3)

The preparation method is the same as that of Example 3, via the condensation reaction of 2-indoleformic acid and 2-tert-butyl-4-methoxyphenol, the yield is 67%. $^1$H NMR (400 MHz, CDCl$_3$) δ (ppm): 1.33 (s, 3H), 3.77 (s, 3H), 7.08-7.11 (m, 1H), 7.16-7.20 (m, 1H), 7.32-7.40 (m, 2H), 7.43-7.44 (m, 1H), 7.74-7.77 (m, 1H),9.36 (s, 1H), $^{13}$C NMR (100 MHz, CDCl$_3$) δ (ppm): 30.1, 34.6, 55.5, 109.9, 110.5, 112.1, 113.9, 121.0, 122.7, 124.6, 125.8, 126.8, 127.4, 137.3, 142.3, 142.7, 157.0, 161.3.

EXAMPLE 32

(2-tert-butyl-4-methoxyphenol) 2-chloro-3-picolinate (XH2038-4)

The preparation method is the same as that of Example 3, via the condensation reaction of 2-chloro-3-picolinic acid and 2-tert-butyl-4-methoxyphenol, the yield is 87%. $^1$H NMR (400 MHz, CDCl$_3$) δ (ppm): 1.34 (s, 9H), 3.83 (s, 3H), 6.79-6.82 (m, 1H), 6.98-6.99 (m, 1H), 7.05-7.07 (m, 1H), 7.43 (m, 1H), 8.37-8.39 (m, 1H),8.61 (s, 1H). $^{13}$C NMR (100 MHz, CDCl$_3$) δ (ppm): 30.2, 34.7, 55.6, 110.9, 114.1, 122.4, 124.5, 126.7, 140.5, 142.5, 142.6, 150.7, 152.5, 157.4, 163.7.

EXAMPLE 33

(2-tert-butyl-4-methoxyphenol) 2-thiopheneacetate (XH2038-5)

The preparation method is the same as that of Example 3, via the condensation reaction of 2-thiopheneacetic acid and 2-tert-butyl-4-methoxyphenol, the yield is 70%. $^1$H NMR (400 MHz, CDCl$_3$) δ (ppm): 1.27 (s, 9H), 3.78 (s, 3H), 4.10 (s, 2H), 6.70-6.73 (m, 1H), 6.87 (m, 1H), 6.90-0.92 (m, 2H), 6.98-7.07 (m, 1H), 7.04-7.06 (m, 2H),7.24 (m, 1H). $^{13}$C NMR (100 MHz, CDCl$_3$) δ (ppm): 30.1, 34.6, 36.1, 55.5, 110.6, 113.9, 124.4, 125.4, 127.1, 127.5, 134.2, 142.4, 142.8, 157.0, 169.4.

EXAMPLE 34

(2-tert-butyl-4-methoxyphenol) 3-(4-methylphenyl)-propionate (XH2039-1)

The preparation method is the same as that of Example 3, via the condensation reaction of 3-(4-methylphenyl)-propionic acid and 2-tert-butyl-4-methoxyphenol, the yield is 65%. $^1$H NMR (400 MHz, CDCl$_3$) δ (ppm): 1.29 (s, 9H), 2.32 (s, 3H), 2.88-2.90 (t, J=8.2 Hz, 2H), 3.03-3.05 (t, J=8.2 Hz, 2H), 3.78 (s, 3H), 6.69-6.72 (m, 1H), 6.81-6.84 (m, 1H), 6.90-.92 (m, 1H), 7.12-7.15 (m, 4H). $^{13}$C NMR (100 MHz, CDCl$_3$) δ (ppm): 21.0, 30.3, 34.5, 36.6, 55.4, 110.4, 113.7, 124.4, 128.3, 129.2, 135.8, 137.0, 142.2, 142.6, 156.7, 171.8.

EXAMPLE 35

(2-tert-butyl-4-methoxyphenol) 2-phenyl propionate (XH2039-3)

The preparation method is the same as that of Example 3, via the condensation reaction of 2-phenylpropionic acid and 2-tert-butyl-4-methoxyphenol, the yield is 65%. $^1$H NMR (400 MHz, CDCl$_3$) δ (ppm): 1.16 (s, 9H), 1.63-1.67 (d, J=8.8 Hz, 3H), 3.76 (s, 3H), 3.93-3.97 (q, J=8.8 Hz, 1H), 6.68-6.70 (m, 2H), 6.75-6.77 (m, 1H), 6.87-6.88 (m, 1H), 7.20-7.45 (m, 5H). $^{13}$C NMR (100 MHz, CDCl$_3$) δ (ppm): 18.1, 29.7, 34.4, 46.1, 55.4, 110.4, 113.6, 124.1, 127.4, 127.8, 128.7, 139.5, 142.3, 142.9, 156.7, 173.3.

EXAMPLE 36

(2-tert-butyl-4-methoxyphenol) 2-fluoropropionate (XH2039-4)

The preparation method is the same as that of Example 3,via the condensation reaction of 2-fluoropropionic acid and 2-tert-butyl-4-methoxyphenol, the yield is 60%. $^1$H NMR (400 MHz, CDCl$_3$) δ (ppm): 1.33 (s, 9H), 1.72-1.80 (m, 3H), 3.80 (s, 3H), 5.19-5.31 (m, 1H), 6.73-6.76 (m, 1H),6.92-6.95 (m, 2H). $^{13}$C NMR (100 MHz, CDCl$_3$) δ (ppm): 18.0, 18.2, 29.9, 34.6, 55.4, 84.9, 86.7, 110.5, 113.9, 123.9, 142.0, 142.3, 157.1, 169.4.

EXAMPLE 37

(2-tert-butyl-4-methoxyphenol) cyclohexylacetate (XH2039-5)

The preparation method is the same as that of Example 3,via the condensation reaction of cyclohexylacetic acid and 2-tert-butyl-4-methoxyphenol, the yield is 68%. $^1$H NMR (400 MHz, CDCl$_3$) δ (ppm): 1.00-1.20 (m, 3H), 1.20-1.40 (m, 11H), 1.63-1.76 (m, 3H), 1.90-2.00 (m, 1H), 1.83-1.87 (m, 2H), 2.44-2.46 (m, 2H), 3.77 (s, 3H), 6.70-6.73 (m, 1H),6.88-6.92 (m, 2H). $^{13}$C NMR (100 MHz, CDCl$_3$) δ (ppm): 26.0, 26.1, 30.0, 33.1, 34.5, 34.6, 42.6, 55.4, 110.4, 113.7, 124.5, 142.2, 142.7, 156.6, 171.9.

EXAMPLE 38

(2-tert-butyl-4-methoxyphenol) cyclopentanecarboxylate (XH2039-6)

The preparation method is the same as that of Example 3,via the condensation reaction of cyclopentyl formic acid and 2-tert-butyl-4-methoxyphenol, the yield is 78%. $^1$H NMR (400 MHz, CDCl$_3$) δ (ppm): 1.33 (s, 9H), 1.63-1.70 (m, 2H), 1.74-1.82 (m, 2H), 1.93-2.07 (m, 4H), 3.78 (s, 3H), 6.71-6.73 (m, 1H), 6.86-6.88 (d, J=8.8 Hz, 1H), 6.91-6.92 (d, J=2.8 Hz, 1H). $^{13}$C NMR (100 MHz, CDCl$_3$) δ (ppm): 25.7, 29.9, 34.5, 44.4, 55.4, 110.4, 113.6, 124.4, 142.2, 142.9, 156.6, 175.6.

EXAMPLE 39

(2-tert-butyl-4-methoxyphenol) adamantaneacetate (XH2040-1)

The preparation method is the same as that of Example 3, via the condensation reaction of adamantaneacetic acid and 2-tert-butyl-4-methoxyphenol, the yield is 70%. $^1$H NMR (400 MHz, CDCl$_3$) δ (ppm): 1.32 (s, 9H), 1.66-1.76 (m, 12H), 2.01 (br s, 3H), 2.32 (s, 2H), 3.79 (s, 3H), 6.71-6.74 (m, 1H), 6.91-6.94 (m, 2H). $^{13}$C NMR (100 MHz, CDCl$_3$) δ (ppm): 28.7, 30.1, 33.3, 34.6, 36.8, 42.6, 49.2, 55.6, 110.5, 113.8, 124.6, 142.4, 142.7, 156.8, 170.8.

EXAMPLE 40

(2-tert-butyl-4-methoxyphenol) cyclopropylacetate (XH2040-2)

The preparation method is the same as that of Example 3, via the condensation reaction of cyclopropylacetic acid and 2-tert-butyl-4-methoxyphenol, the yield is 73%. $^1$H NMR (400 MHz, CDCl$_3$) δ (ppm): 0.25-0.29 (m, 2H), 0.61-0.66 (m, 2H), 1.19-1.23 (m, 1H), 1.33 (s, 9H), 2.47-2.49 (d, J=7.2 Hz, 2H), 3.79 (s, 3H), 6.72-6.75 (m, 1H), 6.91-6.93 (m, 2H). $^{13}$C NMR (100 MHz, CDCl$_3$) δ (ppm): 4.77, 6.92, 30.1, 40.2, 55.6, 110.6, 113.9, 124.7, 142.4, 142.9, 156.9, 172.2.

EXAMPLE 41

(2-tert-butyl-4-methoxyphenol) N-tert-butoxycarbonylpiperidine-4-formate (XH2040-3)

The preparation method is the same as that of Example 3, via the condensation reaction of N-tert-butoxycarbonylpiperidine-4-formic acid and 2-tert-butyl-4-methoxyphenol, the yield is 73%. $^1$H NMR (400 MHz, CDCl$_3$) δ (ppm): 1.32 (s, 9H), 1.47 (s, 9H), 1.73-1.84 (m, 2H), 2.05-2.10 (m, 2H), 2.66-2.73 (m, 1H), 2.85-2.93 (m, 2H), 3.79 (s, 3H), 4.11-4.16 (m, 2H), 6.71-6.74 (m, 1H), 6.82-6.84 (d, J=8.8 Hz, 1H), 6.92-6.93 (d, J=3.2 Hz, 1H). $^{13}$C NMR (100 MHz, CDCl$_3$) (ppm): 28.0, 28.5, 30.1, 34.7, 41.8, 43.4, 55.6, 79.8, 110.7, 113.8, 124.5, 142.3, 142.8, 154.7, 156.9, 173.7.

EXAMPLE 42

(2-tert-butyl-4-methoxyphenol) octanoate (XH2040-4)

The preparation method is the same as that of Example 3, via the condensation reaction of octanoic acid and 2-tert-butyl-4-methoxyphenol, the yield is 63%. $^1$H NMR (400 MHz, CDCl$_3$) δ (ppm): 0.87-0.91 (m, 3H), 1.27-1.43 (m, 18H), 1.73-1.81 (m, 2H), 2.55-2.59 (t, J=7.6 Hz, 2H), 6.71-6.74 (m, 1H), 6.88-6.90 (d, J=8.8 Hz, 1H), 6.92-6.93 (d, J=3.2 Hz, 1H). $^{13}$C NMR (100 MHz, CDCl$_3$) δ (ppm): 14.2, 22.7, 24.9, 29.0, 29.3, 30.1, 31.8, 34.7, 35.0, 55.6, 110.5, 113.8, 124.6, 142.3, 142.8, 156.8, 172.9.

EXAMPLE 43

(2-tert-butyl-4-methoxyphenol) 7-oxooctanoate (XH2040-5)

The preparation method is the same as that of Example 3, via the condensation reaction of 7-oxooctanoic acid and 2-tert-butyl-4-methoxyphenol, the yield is 60%. $^1$H NMR (400 MHz, CDCl$_3$) δ (ppm): 1.30-1.44 (m, 13H), 1.60-1.66 (m, 2H), 1.74-1.80 (m, 2H), 2.16 (s, 3H), 2.45-2.49 (t, J=7.2 Hz, 2H), 2.57-2.60 (t, J=7.6 Hz, 2H), 3.79 (s, 3H), 6.71-6.74 (m, 1H), 6.88-6.90 (d, J=8.8 Hz, 1H), 6.92-6.93 (d, J=3.2 Hz, 1H). $^{13}$C NMR (100 MHz, CDCl$_3$) δ (ppm): 23.4, 24.6, 28.7, 29.5, 30.1, 34.6, 34.7, 43.5, 55.6, 110.6, 111.8, 124.6, 142.3, 142.7, 156.8, 172.6, 209.0.

EXAMPLE 44

(2-tert-butyl-4-methoxyphenol) cyclohexene-2-carboxylate (XH2041-1)

The preparation method is the same as that of Example 3, via the condensation reaction of cyclohexene-2-carboxylic acid and 2-tert-butyl-4-methoxyphenol, the yield is 57%. $^1$H NMR (400 MHz, CDCl$_3$) δ (ppm): 1.31 (s, 9H), 2.78-2.86 (m, 4H), 3.36-3.41 (m, 1H), 3.79 (s, 3H), 5.72 (s, 2H), 6.71-6.74 (m, 1H), 6.88-6.90 (d, J=8.8 Hz, 1H), 6.92-6.93 (d, J=3.2 Hz, 1H). $^{13}$C NMR (100 MHz, CDCl$_3$) δ (ppm): 30.1, 34.6, 36.2, 42.4, 55.6, 110.6, 113.8, 124.5, 129.1, 142.3, 143.1, 156.8, 175.1.

EXAMPLE 45

(2-tert-butyl-4-methoxyphenol) 2,4,5-trifluorophenylacetate (XH2041-2)

The preparation method is the same as that of Example 3, via the condensation reaction of 2,4,5-trifluorophenylacetic acid and 2-tert-butyl-4-methoxyphenol, the yield is 77%. $^1$H NMR (400 MHz, CDCl$_3$) δ (ppm): 1.27 (s, 9H), 3.78 (s, 3H), 3.87 (s, 2H), 6.71-6.74 (m, 1H), 6.88-6.91 (m, 2H), 6.95-7.01 (m, 1H), 7.19-7.25 (m, 1H). $^{13}$C NMR (100 MHz, CDCl$_3$) δ (ppm): 29.8, 34.4, 55.4, 105.4, 105.6, 105.7, 105.9, 110.5, 113.8, 119.1, 119.3, 124.2, 142.2, 142.5, 157.0, 168.7.

EXAMPLE 46

(2-tert-butyl-4-methoxyphenol) 2-bromo-5-iodo benzoate (XH2041-3)

The preparation method is the same as that of Example 3, via the condensation reaction of 2-bromo-5-iodobenzoic acid and 2-tert-butyl-4-methoxyphenol, the yield is 87%. $^1$H NMR (400 MHz, CDCl$_3$) δ (ppm): 1.34 (s, 9H), 3.82 (s, 3H), 6.78-6.80 (m, 1H), 6.97-6.98 (d, J=2.8 Hz, 1H), 7.05-7.07 (d, J=8.8 Hz, 1H), 7.45-7.47 (d, J=8.4 Hz, 1H), 7.69-7.71 (dd, J1=8.4 Hz, J2=2.0 Hz, 1H), 8.28 (d, J=2.0 Hz, 1H). $^{13}$C NMR (100 MHz, CDCl$_3$) δ (ppm): 30.4, 34.8, 55.7, 92.1, 110.9, 114.2, 122.4, 124.5, 133.7, 136.5, 140.3, 142.1, 142.8, 157.4, 164.1.

EXAMPLE 47

(2-tert-butyl-4-methoxyphenol) 2-fluoro-4-nitryl benzoate (XH2041-4)

The preparation method is the same as that of Example 3, via the condensation reaction of 2-fluoro-4-nitrylbenzoic acid and 2-tert-butyl-4-methoxyphenol, the yield is 85%. $^1$H NMR (400 MHz, CDCl$_3$) δ (ppm): 1.32 (s, 9H), 3.83 (s, 3H), 6.78-6.81 (dd, J1=8.4 Hz, J2=3.2 Hz, 1H), 6.98-6.99 (d, J=3.2 Hz, 1H), 7.02-7.05 (d, J=8.4 Hz, 1H), 8.09-8.12 (dd, J1=9.6 Hz, J2=2.0 Hz, 1H), 8.15-8.18 (m, 1H), 8.30-8.34 (m, 1H). $^{13}$C NMR (100 MHz, CDCl$_3$) δ (ppm): 30.0, 34.5, 55.5, 110.7, 113.1, 113.4, 114.0, 119.1, 123.9, 124.0, 124.3, 133.7, 142.2, 142.4, 151.3, 157.3, 160.3, 162.0, 163.0.

EXAMPLE 48

(2-tert-butyl-4-methoxyphenol) N-tert-butoxycarbonylpiperidine-3-formate (XH2041-5)

The preparation method is the same as that of Example 3, via the condensation reaction of N-tert-butoxycarbonylpiperidine-3-formic acid and 2-tert-butyl-4-methoxyphenol, the yield is 65%. $^1$H NMR (400 MHz, CDCl$_3$) δ (ppm): 1.32 (s, 9H), 1.47 (s, 9H), 1.50-1.67 (m, 2H), 1.76-1.82 (m, 2H), 2.22-2.26 (m, 1H), 2.67-2.73 (m, 1H), 2.82-2.89 (m, 1H), 3.10-3.16 (m, 1H), 3.79 (s, 3H), 3.98-4.01 (m, 1H), 4.33 (br s, 1H), 6.71-6.74 (dd, J1=8.8 Hz, J2=2.8 Hz,1H), 6.83-6.85 (d, J=8.8 Hz, 1H), 6.91-6.92 (d, J=2.8 Hz, 1H). $^{13}$C NMR (100 MHz, CDCl$_3$) δ (ppm): 14.1, 24.2, 27.2, 28.3, 29.4, 30.1, 34.5, 41.8, 55.4, 79.8, 110.5, 113.7, 124.4, 142.2, 142.6, 154.6, 156.8, 172.4.

EXAMPLE 49 di(2-tert-butyl-4-methoxyphenol) p-phenylenediacetate (XH2042)

The preparation method is the same as that of Example 3, via the condensation reaction of p-phenylenediaceticacid (5 mmol) and 2-tert-butyl-4-methoxyphenol (10 mmol), the yield is 65%. $^1$H NMR (400 MHz, CDCl$_3$) δ (ppm): 1.23 (s, 18H), 3.74 (s, 6H), 6.67-6.71(dd, J1=8.8 Hz, J2=3.2 Hz, 2H), 6.83-6.86 (d, J=8.8 Hz, 2H), 6.89-6.90 (d, J=3.2 Hz, 2H), 7.39 (s, 4H). $^{13}$C NMR (100 MHz, CDCl$_3$) δ (ppm): 30.1, 34.6, 41.9, 55.6, 110.7, 114.0, 124.6, 130.1, 132.5, 142.5, 142.9, 157.1, 170.5.

EXAMPLE 50

(2-tert-butyl-4-methoxyphenol) 4-benzoyl butyrate (XH2043-1)

The preparation method is the same as that of Example 3, via the condensation reaction of 4-benzoylbutyric acid and 2-tert-butyl-4-methoxyphenol, the yield is 75%. $^1$H NMR (400 MHz, CDCl$_3$) δ (ppm): 1.32 (s, 9H), 2.20-2.23 (m, 2H), 2.71-2.75 (t, J=8.8 Hz, 2H), 3.14-3.17 (t, J=7.0 Hz, 2H), 3.79 (s, 3H), 6.72-6.75 (m, 1H), 6.91-6.93 (m, 2H), 7.44-7.49 (m, 2H), 7.55-7.59 (m, 1H), 7.97-7.99 (m, 2H). $^{13}$C NMR (100 MHz, CDCl$_3$) δ (ppm): 19.4, 30.2, 34.1, 34.7, 37.6, 55.7, 110.7, 114.0, 124.7, 128.2, 128.9, 133.4, 136.9, 142.4, 142.8, 157.0, 172.5, 199.6.

EXAMPLE 51

(2-tert-butyl-4-methoxyphenol) 3,5-dimethoxy phenylacrylate (XH2043-2)

The preparation method is the same as that of Example 3, via the condensation reaction of 3,5-dimethoxyphenylacrylic acid and 2-tert-butyl-4-methoxyphenol, the yield is 60%. $^1$H NMR (400 MHz, CDCl$_3$) δ (ppm): 1.35 (s, 9H), 3.81 (s, 3H), 6.53-6.54 (t, J=2.3 Hz, 1H), 6.61-6.65 (d, J=16 Hz, 1H), 6.73-6.78 (m, 3H), 6.95-7.00 (m, 2H), 7.77-7.81 (d, J=16 Hz, 1H). $^{13}$C NMR (100 MHz, CDCl$_3$) δ (ppm): 30.3, 34.8, 55.7, 103.1, 106.4, 110.7, 114.0, 118.4, 124.8, 136.2, 142.7, 146.8, 157.1, 161.3, 166.2.

EXAMPLE 52

(2-tert-butyl-4-methoxyphenol) 4-chloropyridine-2-formate (XH2043-3)

The preparation method is the same as that of Example 3, via the condensation reaction of 4-chloropyridine-2-formic acid and 2-tert-butyl-4-methoxyphenol, the yield is 65%. $^1$H NMR (400 MHz, CDCl$_3$) δ (ppm): 1.36 (s, 9H), 3.82 (s, 3H), 6.78-6.81 (dd, J1=9.2 Hz, J2=3.0 Hz, 1H), 6.98-6.99 (d, J=3.0 Hz, 1H), 7.04-7.06 (d, J=9.2 Hz, 1H), 7.56-7.58 (dd, J1=5.2 Hz, J2=2.3 Hz, 1H), 8.27-8.28 (m, 1H), 8.75-8.76 (d, J=5.2 Hz, 1H). $^{13}$C NMR (100 MHz, CDCl$_3$) δ (ppm): 30.4, 34.9, 55.7, 110.9, 114.2, 124.6, 126.4, 127.7, 142.8, 145.8, 149.3, 151.3, 157.4, 163.7.

EXAMPLE 53

(2-tert-butyl-4-methoxyphenol) N-methylpiperidine-3-formate (XH2043-4)

The preparation method is the same as that of Example 3, via the condensation reaction of N-methylpiperidine-3-formic acid and 2-tert-butyl-4-methoxyphenol, the yield is 60%. $^1$H NMR (400 MHz, CDCl$_3$) δ (ppm): 1.34 (s, 9H), 1.51-1.61 (m, 1H), 1.65-1.74 (m, 1H), 1.80-1.85 (m, 1H), 1.99-2.05 (m, 1H), 2.13-2.18 (m, 1H), 2.24-2.31 (m, 1H), 2.34 (s, 3H), 2.79-2.92 (m, 2H), 3.14-3.16 (br d, 1H), 3.78 (s, 3H), 6.70-6.74 (dd, J1=8.4 Hz, J2=3.2 Hz, 1H), 6.84-6.86 (d, J=8.4 Hz, 1H). $^{13}$C NMR (100 MHz, CDCl$_3$) δ (ppm): 24.6, 26.3, 29.9, 34.5, 42.3, 46.4, 55.4, 55.5, 57.1, 110.5, 113.7, 124.4, 142.2, 142.6, 156.7, 172.9.

EXAMPLE 54

(2-tert-butyl-4-methoxyphenol) N-tert-butoxycarbonyl-6-amino pentanoate (XH2043-5)

The preparation method is the same as that of Example 3, via the condensation reaction of N-tert-butoxycarbonyl-6-amino pentanoic acid and 2-tert-butyl-4-methoxyphenol, the yield is 60%. $^1$H NMR (400 MHz, CDCl$_3$) δ (ppm): 1.32 (s, 9H), 1.45 (s, 9H), 1.57-1.65 (m, 2H), 1.75-1.83 (m, 2H), 2.59 (t, J=7.6 Hz, 2H), 3.16-3.19 (t, J=6.8 Hz, 2H), 3.79 (s, 3H), 6.71-6.74 (dd, J1=8.8 Hz, J2=2.8 Hz, 1H), 6.87-6.89 (d, J=8.8 Hz, 1H), 6.92-6.93 (d, J=2.8 Hz, 1H). $^{13}$C NMR (100 MHz, CDCl$_3$) δ (ppm): 22.1, 28.6, 29.8, 30.2, 34.6, 34.8, 40.4, 55.7, 110.7, 114.0, 124.7, 142.5, 142.9, 156.2, 157.0, 172.6.

EXAMPLE 55

(2-tert-butyl-4-methoxyphenol) 3,3,3-trifluoropropionate (XH2044-1)

The preparation method is the same as that of Example 3, via the condensation reaction of 3,3,3-trifluoropropionic acid and 2-tert-butyl-4-methoxyphenol, the yield is 60%. $^1$H NMR (400 MHz, CDCl$_3$) δ (ppm): 1.33 (s, 9H), 3.41-3.48 (q, J=19.9 Hz, 2H), 3.79 (s, 3H), 6.72-6.75 (m, 1H), 6.91-6.94 (m, 2H). $^{13}$C NMR (100 MHz, CDCl$_3$) δ (ppm):30.2, 34.8, 40.3, 55.7, 110.9, 114.2, 124.4, 142.5, 157.5, 163.5.

EXAMPLE 56

(2-tert-butyl-4-methoxyphenol) morpholin-4-yl acetate (XH2044-2)

The preparation method is the same as that of Example 3, via the condensation reaction of morpholin-4-yl acetic acid and 2-tert-butyl-4-methoxyphenol, the yield is 68%. $^1$H NMR (400 MHz, CDCl$_3$) δ: 1.30 (s, 9H), 2.65-2.68 (t, J=4.4 Hz, 4H), 3.47 (s, 2H), 3.75-3.79 (m, 7H), 6.70-6.73 (m, 1H), 6.89-6.92 (m, 2H). $^{13}$C NMR (100 MHz, CDCl$_3$) δ (ppm): 30.3, 34.7, 53.5, 55.7, 60.2, 67.0, 110.7, 114.1, 124.6, 142.4, 157.1, 169.2.

EXAMPLE 57

(2-tert-butyl-4-methoxyphenol) 3-(3,5-di-tert-butyl-4-hydroxy-phenyl)propionate (XH2045-2)

The preparation method is the same as that of Example 3, via the condensation reaction of 3-(3,5-di-tert-butyl-4-hydroxy-phenyl)propionic acid and 2-tert-butyl-4-methoxyphenol, the yield is 68%. $^1$H NMR (400 MHz, CDCl$_3$) δ (ppm): 1.29 (s, 9H), 1.45 (s, 18H), 2.86-2.90 (m, 2H), 2.99-3.03 (m, 2H), 3.78 (s, 3H), 5.10 (br s, 1H), 6.69-6.72 (m, 1H), 6.80-6.83 (d, J=8.8 Hz, 1H), 6.90-6.91 (d, J=3.0 Hz, 1H), 7.06 (s, 2H). $^{13}$C NMR (100 MHz, CDCl$_3$) δ (ppm): 30.0, 30.2, 30.8, 34.2, 34.5, 37.0, 55.4, 110.4, 113.7, 124.5, 124.9, 130.7, 135.9, 142.2, 142.7, 152.3, 156.7, 172.1.

EXAMPLE 58 di(2-tert-butyl-4-methoxyphenol) adipate (XH2046-3)

The preparation method is the same as that of Example 3, via the condensation reaction of adipicacid (5 mmol) and 2-tert-butyl-4-methoxyphenol (10 mmol), the yield is 65%. $^1$H NMR (400 MHz, CDCl$_3$) δ (ppm): 1.32 (s, 18H), 1.89-1.93 (m, 4H), 2.64-2.68 (m, 4H), 3.79 (s, 6H), 6.71-6.74 (m, 2H), 6.89-6.93 (m, 4H). $^{13}$C NMR (100 MHz, CDCl$_3$) δ (ppm): 24.3, 30.1, 34.6, 55.6, 110.6, 113.9, 124.6, 142.4, 142.7, 156.9, 172.3.

EXAMPLE 59

(2-tert-butyl-4-methoxyphenol-oxyl) methyl carbonate isopropyl ester (XJP2005)

Dissolving 2-tert-butyl-4-methoxyphenol (5 mmol) in tetrahydrofuran (15 mL), and dropwise adding to the solution of sodium hydride (5.5 mmol)/tetrahydrofuran (10 mL), thereafter, stirring for 30 minutes. Dropwise adding chloromethyl isopropyl carbonate (5 mmol), and then reacting for 24 hours at room temperature. The colourless oily matter is obtained through purification by column chromatography (ethyl acetate:petroleum ether=1:9), the yield is 75%. $^1$H-NMR (CDCl$_3$) δ (ppm): (ppm) 1.32 (s, 9H), 1.35 (d, J=6.4 Hz, 6H), 3.78 (s, 3H), 4.31 (m, 1H), 5.26 (s, 2H), 6.71-6.74 (m, 1H), 6.90-6.91 (d, J=3.0 Hz, 1H), 6.96-6.97 (d, J=8.6 Hz, 1H).

EXAMPLE 60

N-(2-tert-butyl-4-methoxyphenol-oxycarbonyl)glycine ethyl ester (XJP2006)

Dissolving glycine ethyl ester (5.10 mmol) in 100 mL dichloromethane, adding saturated sodium hydrocarbonate solution, stirring in ice-water bath for 5 min. Then adding triphosgene (530 mg, 1.786 mmol), stirring intensely for 15 min. The D-aspartic acid benzyl ester isocyanate (1-1) is obtained by extracting with dichloromethane for four times, drying with anhydrous $Na_2SO_4$ for 1 h, and concentrating to dryness by distillation under reduced pressure. Adding 2-tert-butyl-4-methoxyphenol (1.28 mmol) to 100 mL anhydrous tetrahydrofuran, adding triethylamine (386 mg, 3.83 mmol), stirring for 30 min at room temperature, dissolving the above prepared isocyanate (1-1) with 2 mL dichloromethane, adding to the reaction liquid, raising the temperature to 40° C., stirring for overnight. Quenched the reaction, directly mixed with silica gel, and then evaporated to dryness by distillation, purifying by silica gel column chromatography (ethyl acetate:petroleum ether=1:3). The colourless oily matter is obtained, the yield is 56.8%. $^1$H-NMR (CDCl$_3$) δ (ppm): (ppm) 1.28-1.32 (t, J=7.0 Hz, 3H), 1.34 (s, 9H), 3.79 (s, 3H), 4.06-4.08 (d, J=5.3 Hz, 2H), 4.22-4.28 (q, J=7.0 Hz, 2H), 5.53-5.56 (t, J=5.3 Hz, 1H), 6.71-6.74 (m, 1H), 6.90-6.91 (d, J=3.0 Hz, 1H), 6.96-6.97 (d, J=8.6 Hz, 1H).

EXAMPLE 61

2-(2-tert-butyl-4-methoxyphenoxy) ethyl acetate (XJP1005)

Dissolving 2-tert-butyl-4-methoxyphenol (5 mmol) in tetrahydrofuran(15 mL), then dropwise adding to the solution of sodium hydride (5.5 mmol)/tetrahydrofuran(10 mL), then stirring for 30 minutes. Dropwise adding ethyl bromoacetate (5 mmol), and then reacting for 24 hours at room temperature. The colourless oily matter is obtained through purification by column chromatography (ethyl acetate:petroleum ether=1:9), the yield is 75%. $^1$H-NMR (CDCl$_3$) δ: (ppm) 1.28-1.32 (t, J=7.2 Hz, 3H), 1.40 (s, 9H), 3.77 (s, 3H), 4.24-4.30 (q, J=7.2 Hz, 2H), 4.59 (s, 2H), 6.65-6.66 (m, 2H), 6.88-6.91 (m, 1H).

EXAMPLE 62

Preparation of (2-tert-butyl-4-methoxyphenol) (N-benzyl)carbamate (ZXY1025-2)

Dissolving 2-tert-butyl-4-methoxyphenol (0.9 g, 5 mmol) in dichloromethane (15 mL), adding triethylamine (0.1 mL), dropwise adding the solution of benzyl isocyanate (5 mmol)/dichloromethane (10 mL), then stirring and reacting for 4-10 hours, washing with water, and white solid can be obtained from column chromatography, the yield is 85%. $^1$H-NMR (CDCl$_3$) δ (ppm) 1.32 (s, 3H), 3.78 (s, 3H), 4.47-4.48 (d, J=2.2 Hz, 2H), 5.32-5.34 (br t, J=2.2 Hz, 1H), 6.71-6.74 (m, 1H), 6.89-6.90 (d, J=3.2 Hz, 1H), 6.98-7.01 (d, J=8.4 Hz, 1H), 7.30-7.38 (m, 5H).

EXAMPLE 63

Preparation of (2-tert-butyl-4-methoxyphenol) (N-n-butyl)carbamate (ZXY1025-3)

The preparation method is the same as that of Example 62, which is prepared from the reaction of 2-tert-butyl-4-methoxyphenol and butyl isocyanate, the yield is 90%. $^1$H-NMR (CDCl$_3$) δ (ppm) 0.92-0.95 (t, J=8.0 Hz, 3H), 1.32-1.41 (m, 11H), 1.51-1.58 (m, 2H), 3.25-3.30 (q, J=6.8 Hz, 2H), 3.78 (s, 3H), 4.99 (br t, 1H), 6.70-6.73 (m, 1H), 6.88-6.89 (d, J=3.2 Hz, 1H), 6.94-6.97 (d, J=8.8 Hz, 1H).

EXAMPLE 64

(2-tert-butyl-4-methoxyphenol) (N-isopropyl)carbamate (ZXY1025-4)

The preparation method is the same as that of Example 62, and the yield is 85%. $^1$H-NMR (CDCl$_3$) δ (ppm) 1.21-1.23 (d, J=6.4 Hz, 6H), 1.32 (s, 9H), 3.78 (s, 3H), 3.88-3.93 (m, 1H), 4.82-4.84 (br d, J=8.0 Hz, 1H), 6.70-6.73 (m, 1H), 6.88-6.89 (d, J=3.2 Hz, 1H), 6.94-6.97 (d, J=8.8 Hz, 1H).

EXAMPLE 65

(2-tert-butyl-4-methoxyphenol) (N-cyclohexyl)carbamate (ZXY1025-5)

The preparation method is the same as that of Example 62, and the yield is 87%. $^1$H-NMR (CDCl$_3$) δ (ppm) 1.13-1.25 (m, 2H), 1.32-1.42 (m, 12H), 1.60-1.64 (m, 1H), 1.72-1.75 (m, 2H), 1.99-2.03 (m, 2H), 3.54-3.61 (m, 1H), 3.78 (s, 3H), 4.87-4.89 (d, J=8.4 Hz, 1H), 6.70-6.73 (m, 1H), 6.88-6.89 (d, J=2.0 Hz, 1H), 6.95-6.97 (d, J=8.4 Hz, 1H).

EXAMPLE 66

(2-tert-butyl-4-methoxyphenol) (N-phenethyl)carbamate (ZXY1025-6)

The preparation method is the same as that of Example 62, and the yield is 87%. $^1$H-NMR (CDCl$_3$) δ (ppm) 1.30 (s, 9H), 2.87-2.90 (t, J=6.4 Hz, 2H), 3.52-3.57 (m, 2H), 3.77 (s, 3H), 5.03 (m, 1H), 6.69-6.72 (m, 1H), 6.88-6.94 (m, 2H), 7.22-7.25 (m, 3H), 7.30-7.34 (m, 2H).

EXAMPLE 67

Pivaloyl(2-tert-butyl-4-methoxyphenol-oxyl) methyl ester (XJP1041)

Dissolving 2-tert-butyl-4-methoxyphenol (5 mmol) in tetrahydrofuran (15 mL), then dropwise adding the solution of sodium hydride (5.5 mmol)/tetrahydrofuran (10 mL), and then stirring for 30 minutes. Dropwise adding pivaloy chloride methyl ester (5 mmol), and then reacting for 24 hours at room temperature. The off-white solid can be obtained by purifying with column chromatography (ethyl acetate:petroleum ether=1:9), the yield is 75%. $^1$H-NMR (CDCl$_3$) δ (ppm) 1.24 (s, 9H), 1.32 (s, 9H), 3.78 (s, 3H), 5.30 (s, 2H), 6.69-6.72 (m, 1H), 6.88-6.94 (m, 2H).

EXAMPLE 68

Evaluation the Release Effect of the Compound In Vitro

1. Analysis Conditions
Mobile phase: gradient elution; A: water; B: methanol;
Chromatographic column: CAPCEL PAK MF PH-1;
Detecting instrument: TQ-S; ion source: APCI; ion detection mode: MRM;

2. Releasing Tests of Target Compound in PBS (pH=7.4)

Dissolving a certain amount of the compound in the PBS, vortex blending, dividing into 10 parts equally based on 0.3 mL per part. Incubating at 37° C., taking sample at different time(Oh, 1 h, 2 h, 6 h, 12 h, 24 h and 48 h, etc.), followed with HPLC detection. Calculating the release rate of the drugs by the peak area of the target compound at Oh as a standard. Comparing the peak area of the compounds at other time points with the standard peak area. The experimental results show that the compounds of all the examples remain stable in the aqueous solution, and no BHA was detected.

3. Release Experiment of Target Compound in Human Plasma

Dissolving the target compound with DMSO, then diluting to 5 μg/mL with the normal saline of 0.9%. The human blank plasma after subpackage is preserved at −70° C., unfreezing in a refrigerator at 4° C. when used. Take 20 μL of the blank plasma, adding 20 μL of the target compound solution as above formulated, vortexing for 15 s, and left it in the water bath at 37° C. Taking samples at the time points of 5 min, 20 min, 40 min, 1.5 h, 3 h, 6 h and 9 h, respectively, with three parallel samples for each time point. Adding 100 μL methanol to the samples at different time points of the water bath, precipitating protein, vortexing for 1 min, centrifugating at low temperature in 13000 r• min−1 for 15 min. Take the supernatant and inject 10 μL for detection.

The results show that all the compounds can release BHA, however, the releasing rate and duration time are different, as shown by FIG. 3.

EXAMPLE 69

Metabolism Experiments of the Drugs in the Rats In Vivo

1. Experimental Method

Intragastric administrating a drug to rats weighing 180-200 g; the administration dosage: 100 mg/kg; administration solution: 2.5 mg/mL (lyase is corn oil); fasting for 12 h before administration, with free drinking. Taking 20 μL plasma of the rat at different blood collecting points. Adding 20 μL deionized water followed with 100 μL methanol, vortexing for 1 min, centrifuging for 15 min at 13000 rpm. taking 10 μL for LC-MS/MSanalysis. There are 11 blood collecting points in total: 0 min, 5 min, 20 min, 40 min, 1 h, 1.5 h, 2 h, 4 h, 8 h, 12 h, 24 h.

2. Analysis for Testing Conditions

Mobile phase: A: water; B: methanol, (binary gradient); Elution conditions are shown by table 1:

TABLE 1

| | Elution conditions | | |
|---|---|---|---|
| time(min) | flow rate(1 mL/min) | A | B |
| 0 | 1 | 65 | 35 |
| 8 | 1 | 30 | 70 |
| 8.1 | 1 | 0 | 100 |
| 9 | 1 | 0 | 100 |
| 9.1 | 1 | 65 | 35 |
| 12 | 1 | 65 | 35 |

Ion source: APCI; ion detection mode: MRM.

3. Experimental Results of Representative Compounds

Figure 4:
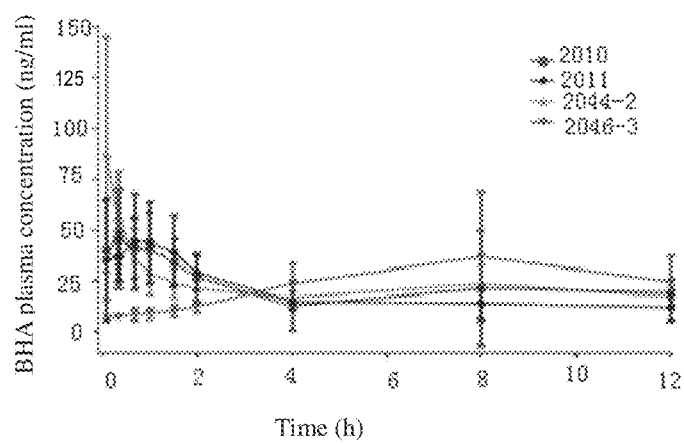
FIG. 4 is a graph illustrating that the compound of the present invention releases BHA in mice in vivo.

According to the experimental results of BHA released in plasma, the compounds with quality metabolic characteristics are selected in the present invention to ensure the metabolic experiments in vivo. The results show that the prodrugs in the present invention can continuously release BHA in vivo (FIG. 4), and the plasma concentration can remain stable for 12 h.

EXAMPLE 70

Test for Cytotoxic Activity

The toxicity of compounds is detected with MTS method in the immortalized mice bone marrowmacrophages (IBMM), mice embryonic fibroblast (NIH3t3) and humanized embryonic nephrocyte. The results show that, the cytotoxicity of the compounds in the examples are all mild, with $IC_{50}$ thereof above 20 mmol , especially the toxicity to macrophages is lower, the security window of the drugs for adjusting differentiation of macrophages is larger (SI>1000). It also can be proved that the anti-tumor effect of the compounds in the examples is irrelevant with the cytotoxicity, which is completely different from the mechanism of the existing anti-tumor drugs. The results are shown in table 2 as follows.

TABLE 2

Experimental results of cytotoxicity of some of the compounds

| | $IC_{50}$(mM) | | |
|---|---|---|---|
| compound code | IBMM cell | NIH3T3 cell | HEK293 cell |
| BHA | 218 | 267 | 325 |
| XH2005 | 439 | 87.5 | 82 |
| XH2006 | 443 | 21.0 | 118 |
| XH2010 | 175 | 186. | 207 |
| XH2011 | 119 | 32.6 | 311 |
| XH2015 | 147 | 194. | 109 |
| XH2016 | 148 | 18.6 | 65 |
| XH2017 | 560 | 22.9 | 8 |
| XH2018 | 130 | 333 | 386 |
| XH2019 | 24 | 47.6 | 37 |
| XH2020 | >700 | 689 | >700 |
| XH2021 | 419 | 281 | >700 |
| XH2022 | 141 | 238 | >700 |
| XH2023 | 6.5 | 65 | 30 |
| XH2024 | 126 | 228 | >700 |
| XH2025 | >700 | >700 | 282 |
| XH2026 | >700 | >700 | >700 |
| XH2027 | 93 | 96 | 177 |
| XH2028 | 156 | 133 | 661 |
| XH2029 | 205 | >700 | 239 |
| XH2030 | 229 | 175 | 151 |
| XH2031 | 218 | 124 | 83 |
| XH2033 | 652 | >700 | >700 |
| XH2034 | 192 | 237 | 190 |
| XH2035 | 202 | 82 | 160 |
| XH2036-1 | 225 | 152 | 160 |
| XH2036-2 | 189 | 205 | 182 |
| XH2036-4 | 230 | 232 | 253 |
| XH2037 | 247 | 256 | 251 |
| XH2038-1 | 222 | 236 | 330 |
| XH2038-2 | 131 | 195 | 257 |
| XH2038-3 | 263 | 517 | 205 |
| XH2038-4 | 122 | 155 | 141 |
| XH2038-5 | 202 | 146 | 266 |
| XH2039-1 | 166 | 223 | 271 |
| XH2039-2 | 159 | 248 | 125 |
| XH2039-3 | 48 | 174 | 188 |
| XH2039-4 | 161 | 233 | 294 |
| XH2039-5 | 67 | 106 | 87 |
| XH2039-6 | 171 | 229 | 136 |
| XH2040-1 | 55 | 132 | 129 |
| XH2040-2 | 202 | 232 | 237 |
| XH2040-3 | 115 | 151 | 287 |
| XH2040-4 | 198 | 366 | 283 |

TABLE 2-continued

Experimental results of cytotoxicity of some of the compounds

| compound code | IC$_{50}$(mM) | | |
|---|---|---|---|
| | IBMM cell | NIH3T3 cell | HEK293 cell |
| XH2040-5 | 249 | 217 | 342 |
| XH2041-1 | 180 | 140 | 218 |
| XH2041-2 | 156 | 260 | 349 |
| XH2041-3 | 60 | 139 | 279 |
| XH2041-4 | 224 | 173 | >700 |
| XH2041-5 | 51 | 171 | 67 |
| XH2042 | 388 | >700 | 61 |
| XH2043-1 | 409 | >700 | 279 |
| XH2043-2 | 100 | 365 | >700 |
| XH2043-3 | 331 | 106 | >700 |
| XH2043-4 | 146 | 132 | >700 |
| XH2043-5 | 97 | 157 | 377 |
| XH2044-1 | >700 | 353 | 206 |
| XH2044-2 | 561 | >700 | 125 |
| XH2045-2 | 154 | 142 | 111 |
| XH2046-3 | 352 | >700 | >700 |
| XJP2006 | 92 | 300 | 176 |
| XJP2005 | 309 | 171 | >700 |

EXAMPLE 71

Experiments of Acute Toxicity in Mice

1. Experimental Method

Detecting the acute toxicity of some of the compounds by using up-down method. Intragastric administrating a drug to the mice of 20~22 g; lyase is corn oil, fasting for 12 h before administration, with free drinking.

2. Experimental Results

The results are shown in table 3, which identified with the experimental results of cytotoxicity. The acute toxicity of the representative compounds XH2006, XH2010, XH2011 and XH2044-2 prepared by the present invention are all lower than that of 2-tert-butyl-4-methoxyphenol-oxyl (BHA), indicating better safety.

TABLE 3

Experimental results of acute toxicity in mice of some compounds

| compound | LD$_{50}$ |
|---|---|
| BHA | 1100 |
| XH2006 | >1200 |
| XH2010 | >1200 |
| XH2011 | >1300 |
| XH2044-2 | >1300 |

INDUSTRIAL APPLICATION

The advantages of the present invention lie in: 1) the compound provided by the present invention can slowly release 2-tert-butyl-4-methoxyphenol in vivo, overcoming the disadvantage that the half-life of 2-tert-butyl-4-methoxyphenol directly administered in the body is short (T1/2=0.5~1 h), and maintains stable plasma concentration of 2-tert-butyl-4-methoxyphenol (T1/2=12~24 h). 2) The equivalent dose of the compound provided by the present invention is lower, and for achieving the same plasma concentration and the curve of similar drugs (AUC), the administrating dose of the compound of the present invention is merely 1/100 1/5000 of the directly administered dose of 2-tert-butyl-4-methoxyphenol, avoiding the toxic effect resulted from 2-tert-butyl-4-methoxyphenol with high dose. 3) the cytotoxicity of the compound provided by the present invention is lower when compared with that of 2-tert-butyl-4-methoxyphenol, and the acute toxicity of part of the compounds in mice (LD$_{50}$>1200mg/kg) is lower than that of 2-tert-butyl-4-methoxyphenol (LD$_{50}$=1100mg/kg). 4)the compound provided by the present invention protects the phenolic hydroxyl group of 2-tert-butyl-4-methoxyphenol, avoids the oxidation in the environment and increases the environmental stability of the drugs.

The invention claimed is:

1. An anti-tumor drug or immunomodulation drug, comprising an effective amount of a compound of formula I,

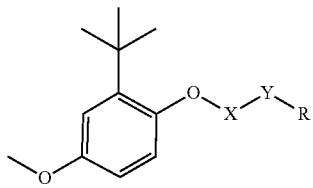

formula I wherein X is C=O; Y is absent; R is selected from any one of the following groups:
1) a substituted or unsubstituted cycloalkyl group having at least three carbon atoms,
2) a substituted or unsubstituted alkenyl group or alkynyl group having at least two carbon atoms, wherein a substituent is an amino group, a nitro group, a carbonyl group, amino acid derivatives, a natural flavorne, a natural alkaloid, a polyethylene glycol, a polyglutamic, acid or a polysaccharide,
3) an unsubstituted aryl or heteroaryl group having at least 4 carbon atoms, wherein the unsubstituted aryl or heteroaryl group is a naphthalene ring, an indole, a pyridine, a purine, a pyrimidine, an imidazole, a furan, or a pyrrole,
4) a substituted aryl or heteroaryl group having at least 4 carbon atoms, wherein the substituted aryl or heteroaryl group is a naphthalene ring, an indole, a purine, a pyrimidine, an imidazole, a furan or a benzoheterocycle, and wherein a substituent is a halo, an amino group, a nitro group, an ester group, a carbonyl group, amino acid derivatives, a natural flavone, a natural alkaloid, a polyethylene glycol, a polyglutamic acid, or polysaccharide,
or pharmaceutically acceptable salts thereof, hydrates thereof, solvates thereof, or a pharmaceutical composition thereof as an active component.

2. The anti-tumor drug or immunomodulation drug of claim 1, wherein the drug releases 2-tert-butyl-4-methyoxyphenyl.

* * * * *